United States Patent [19]

Kaji

[11] Patent Number: 5,443,758
[45] Date of Patent: Aug. 22, 1995

[54] NON-LINEAR OPTICAL MATERIAL CONTAINING STEROIDAL KETONE COMPOUND

[75] Inventor: Makoto Kaji, Hatachi, Japan

[73] Assignee: Hatachi Chemical Company, Ltd., Tokyo, Japan

[21] Appl. No.: 942,153

[22] Filed: Sep. 8, 1992

Related U.S. Application Data

[63] Continuation-in-part of Ser. No. 724,186, Jul. 1, 1991, abandoned.

[30] Foreign Application Priority Data

Jun. 29, 1990 [JP] Japan .................................. 2-172898
Nov. 30, 1990 [JP] Japan .................................. 2-329466

[51] Int. Cl.$^6$ ........................... F21V 9/00; G02F 1/37
[52] U.S. Cl. ..................... 252/582; 252/589; 359/328; 552/526; 552/527; 548/440
[58] Field of Search ................. 552/526, 527; 252/582, 252/587, 589; 385/122; 359/326, 328; 548/440, 445

[56] References Cited

FOREIGN PATENT DOCUMENTS 2417357 10/1975 Germany .

OTHER PUBLICATIONS

Bridgeman, Journal of the Chemical Society (C), pp. 244–250, (1970).
Journal of the Chemical Society. C. No. 11, pp. 1597–1602 (1969).
Journal of the Chemical Society. C. No. 2, pp. 244–250 (1970).
Journal of the Chemical Society. C. No. 8, pp. 1052–1055 (1977).
Comptes Rendus Hebdomadaires des Seances de L'Academie des Sciences, Serie C. vol. 265, No. 17, pp. 929–931 (Oct. 23, 1967).
Tetrahedron, (Incl. Tetrahedron Reports) vol. 34, No. 8, pp. 1179–1186 (1978).
Journal of the Chemical Society. C. No. 4, pp. 492–498 (1972).
Bulletin de la Societe Chimique de France. Pt 2. No. 1–2, pp. 255–259 (1976).
Chemical Abstracts, vol. 72, No. 11, Abstract No. 55740 (1970).
"Nonlinear Optical Properties of Organic Molecules and Crystals", vol. 1, Academic Press Edited by D. S. Chemla, pp. 233–234.

*Primary Examiner*—Philip Tucker
*Attorney, Agent, or Firm*—Antonelli, Terry, Stout & Kraus

[57] ABSTRACT

A steroidal ketone compound having a substituted or unsubstituted aromatic group or heterocyclic aromatic group is useful as a non-linear optical material in a non-linear optical device.

24 Claims, 17 Drawing Sheets

NON-LINEAR OPTICAL MATERIAL CONTAINING STEROIDAL KETONE COMPOUND

CROSS-REFERENCE TO RELATED APPLICATION

This is a continuation-in-part of application Ser. No. 7/724,186, filed on Jul. 1, 1991, now abandoned, the entire contents of which is incorporated herein by reference.

BACKGROUND OF THE INVENTION

The present invention relates to a novel steroidal ketone compound which can be used for an device in optical parametric oscillation, higher harmonic wave generation, electro-optical switching, etc., a process for producing the same, a non-linear optical material and a non-linear optical device.

Non-linear optical materials which are expected to play an important role in the optical communication technology and the like exhibit such functions as optical mixing, optical parametric oscillation, higher harmonic wave generation, electro-optical switching, optical rectification and light-light switching, based on the non-linear optical susceptibility of the materials. Previously, inorganic crystals such as those of $KH_2PO_4$ and $NH_4H_2PO_4$ have been used as such materials. However, these materials are disadvantageous in that their nonlinear optical susceptibility is considerably low for practical use and further they are deliquescent.

Organic non-linear optical materials, which make use of the polarization of the $\pi$ electron system, have a high non-linear optical susceptibility as compared with prior materials, and also are excellent in high-speed response and damage threshold value, so that research and development thereof have been widely forwarded recently in various fields. Recent results of such efforts are described in detail in, for example, "Nonlinear Optical Properties of Organic and Polymeric Materials" (edited by D. J. Williams, ACS Symposium Series No. 233, published by American Chemical Society, Washington, D.C., 1983), "Nonlinear Optical Properties of Organic Molecules and Crystals", Vol. 1 and Vol. 2 (edited by D. S. Chemla and J. Zyss, published by Academic Press, Orlando, Fla., 1987), "Nonlinear Optical and Electroactive Polymers" (edited by P. N. Prasad and D. R. Vlrich, published by Prenum Press, New York, 1987) and "Nonlinear Optical Effects in Organic Polymers" (edited by J. Messier, F. Kajar, P. N. Prasad and D. R. Vlrich, published by Klewer Academic Publishers, Dordrecht, The Netherlands, 1989).

However, no material has yet been found which has a large non-linear optical coefficient of such an extent as enables satisfactory attainment of the purpose in low output lasers as semiconductor lasers. Also, the problem of poor thermal stability, which in a shortcoming common to organic materials, has not been solved. Accordingly, further development of novel materials is eagerly desired.

SUMMARY OF THE INVENTION

An object of the present invention is to provide an organic non-linear optical material having a high non-linear optical coefficient, a novel steroidal ketone compound which enables the production of said material, a process for producing the same, and a non-linear optical device using the same.

The present invention provides a steroidal ketone compound represented by the formula:

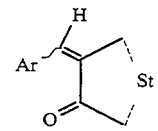

[I]

wherein Ar is a substituted or unsubstituted aromatic group or heterocyclic aromatic group; St is asteroid residue, and the bond shown by ∿ denotes a cis- or trans-position.

The present invention further provides a steroidal ketone compound represented by the formula:

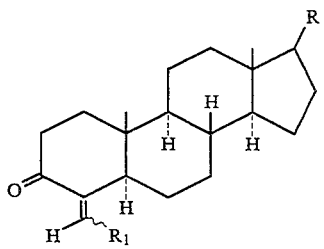

[II]

or the formula:

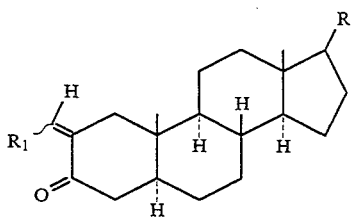

[III]

wherein R is a hydrogen atom or an alkyl group having 1–20 carbon atoms; the bond shown by ∿ denotes a cis- or transposition; and $R_1$ is a substituted or unsubstituted aromatic group, such as

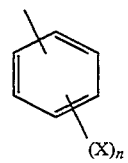

or heterocyclic aromatic group such as

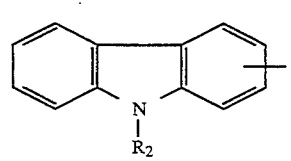

wherein $R_2$ is an alkyl group having 1 to 6 carbon atoms.

The present invention still further provides a steroidal ketone compound represented by the formula:

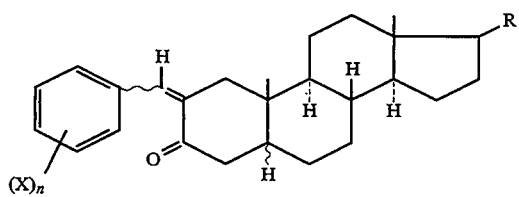

[IV]

or the formula:

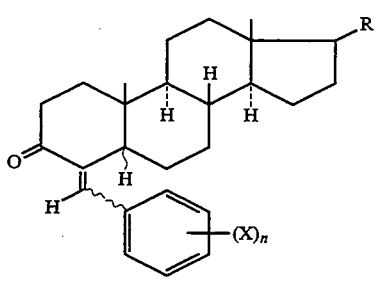

[V]

wherein R is an alkyl group having 1–20 carbon atoms; X is an amino group, an alkylamino group having 1 to 6 carbon atoms, a dialkylamino group having 1 to 6 carbon atoms in each alkyl group, an acylated amino group, a hydroxyl group, an alkoxy group having 1 to 6 carbon atoms, a thioalkyl group having 1 to 6 carbon atoms, an alkyl group having 1–20 carbon atoms, a nitro group, a cyano group, a halogen atom or a hydrogen atom, provided that when n is 2 or more, these groups and atoms may be different from one another; the bond shown by ∼ denotes a cis- or trans-position; and n is an integer of 1 to 5.

The present invention further provides a process for producing a steroidal ketone compound of the formula [I] which comprises reacting a substituted or unsubstituted aromatic aldehyde or heterocyclic aromatic aldehyde with a steroidal ketone compound having an active methylene group.

The present invention still further provides a process for producing a steroidal ketone compound of the formula [II], [III], [IV] or [V] which comprises reacting an aldehyde represented by the formula:

$R_1$—CHO [VI]

wherein $R_1$ is a substituted or unsubstituted aromatic such as

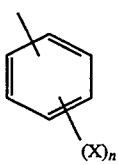

or heterocyclic aromatic group such as

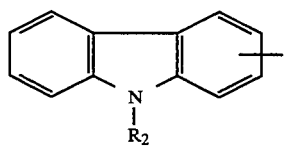

wherein $R_2$, X and n are as defined above, with a steroidal ketone compound having an active methylene group represented by the formula:

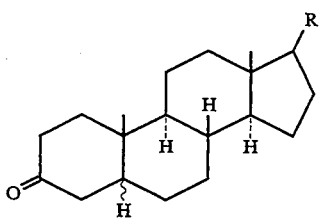

[VII]

wherein R is a hydrogen atom or an alkyl group having 1–20 carbon atoms; and the bond shown by ∼ denotes a cis- or trans-position.

The present invention further provides a non-linear optical material comprising the steroidal ketone compound mentioned above and a non-linear optical element using the non-linear optical material.

DESCRIPTION OF THE PREFERRED EMBODIMENTS

Figure 1:
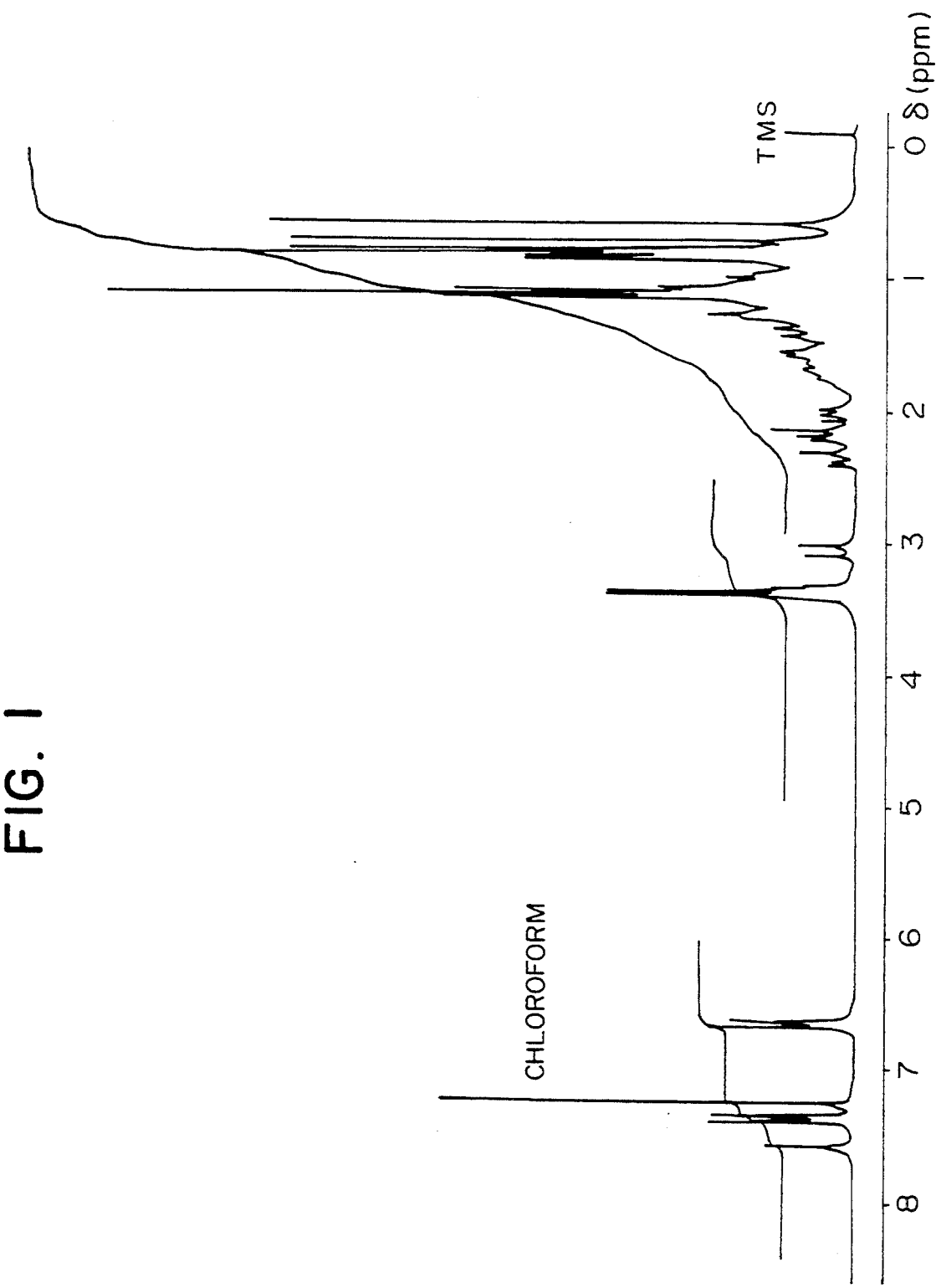
FIG. 1 shows the NMR chart of the steroidal ketone compound 1 obtained in Example 1.

The steroidal ketone compound of the present invention is represented by the formula:

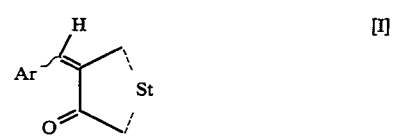

[I]

wherein Ar is a substituted or unsubstituted aromatic group or a heterocyclic aromatic group; St is a steroid residue; and the bond shown by ∼ denotes a cis- or trans-position.

In the present invention, preferred is a steroidal ketone compound represented by the formula [II] or [III]:

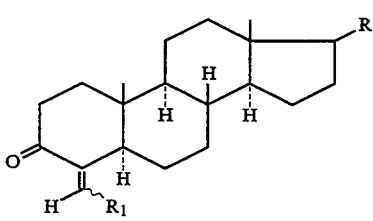

[II]

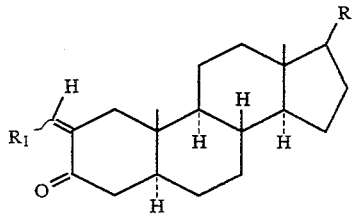

[III]

wherein R is an alkyl group having 1–20 carbon atoms; the bond shown by ∿ denotes a cis- or trans-position; and R₁ is a substituted heterocyclic aromatic group of the formula:

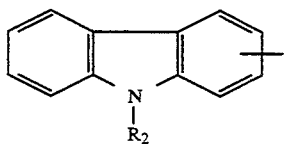

wherein $R_2$ is an alkyl group having 1 to 6 carbon atoms, preferably an ethyl group, or a steroidal ketone compound represented by the formula [IV] or [V]:

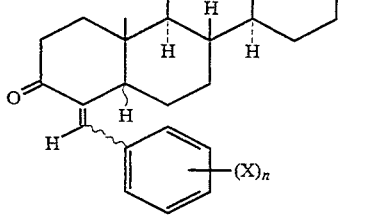

[V]

wherein R is an alkyl group having 1–20 carbon atoms; X is an amino group, an alkylamino group having 1 to 6 carbon atoms, a dialkylamino group having 1 to 6 carbon atoms in each alkyl group, an acylated amino group having 1 to 6 carbon atoms, a hydroxyl group, an alkoxy group having 1 to 6 carbon atoms, a thioalkyl group having 1 to 6 carbon atoms, an alkyl group having 1–20 carbon atoms, a nitro group, a cyano group or a halogen atom, provided that when n is 2 or more these groups and atoms may be different from one another; the bond shown by ∿ denotes a cis- or transposition; and n is an integer of 1 to 5; more preferred is a compound represented by the formula:

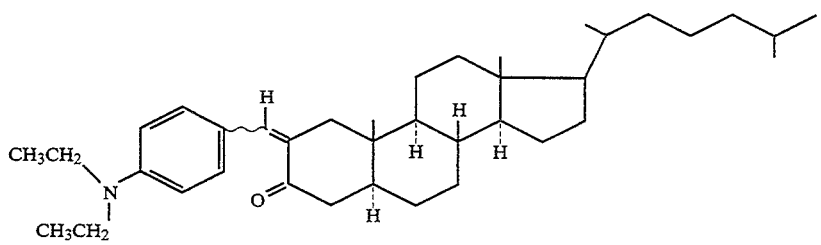

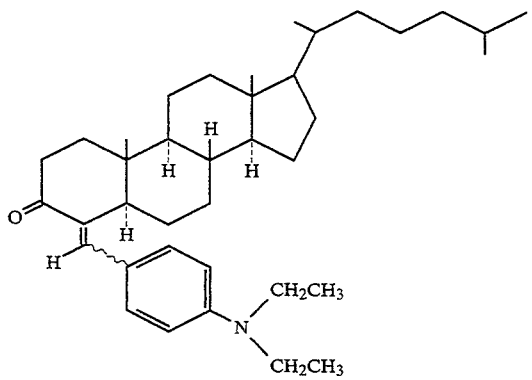

wherein the bond shown by ∿ denotes a cis- or trans-position.

Further, the present invention relates to a process for producing said steroidal ketone compound which comprises reacting a substituted or unsubstituted aromatic aldehyde or heterocyclic aromatic aldehyde with a steroidal ketone compound having an active methylene group, to a non-linear optical material comprising said steroidal ketone compound or a composition containing said steroidal ketone compound, and to a non-linear optical device using said non-linear optical material.

The steroidal ketone compound represented by the formula [I] may be obtained, through an aldol condensation described, for example, collectively in Organic Reaction Vol. 16, by reacting a substituted or unsubsti-

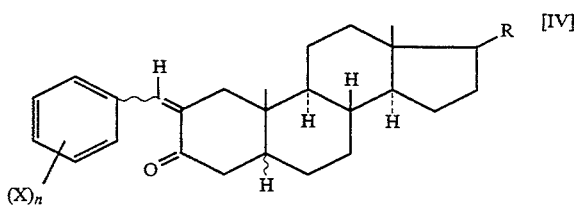

[IV]

tuted aromatic aldehyde or heterocyclic aromatic aldehyde with a steroidal ketone compound having an active methylene group.

The steroidal ketone compound represented by the formula [II], [III], [IV] or [IV] may be obtained, for example, by reacting an aldehyde represented by the formula:

R₁—CHO [VI]

wherein R₁ is a substituted or unsubstituted aromatic such as

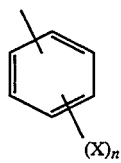

or heterocyclic aromatic group such as

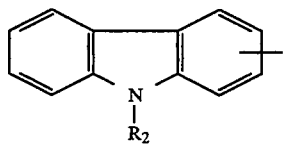

wherein R₂, X and n are as defined above with a steroidal ketone compound having an active methylene group represented by the formula:

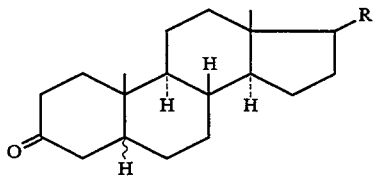

[VII]

wherein R is a hydrogen atom or an alkyl group having 1–20 carbon atoms; and the bond shown by ~ denotes a cis- or trans-position.

Examples of the steroidal ketone compound having an active methylene group are shown below by way of their structural formulas.

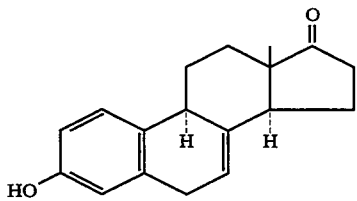

Equilin

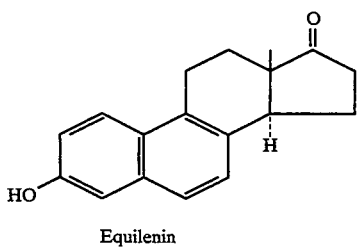

Equilenin

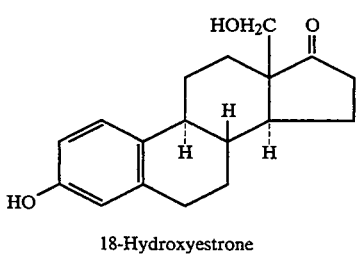

18-Hydroxyestrone

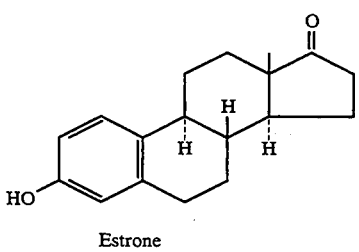

Estrone

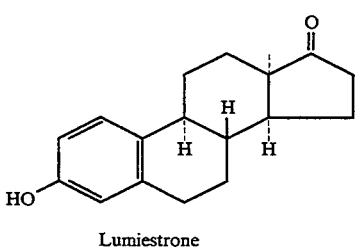

Lumiestrone

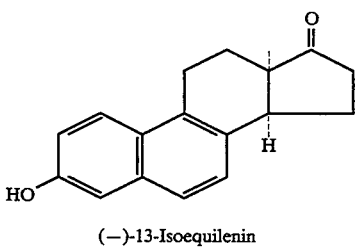

(−)-13-Isoequilenin

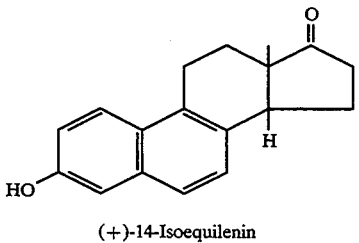

(+)-14-Isoequilenin

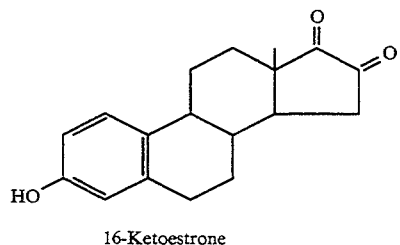
16-Ketoestrone
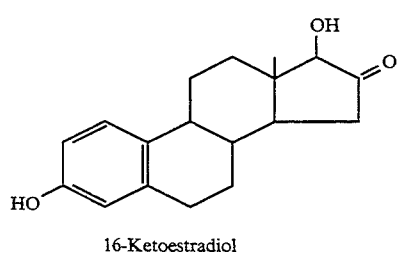
16-Ketoestradiol
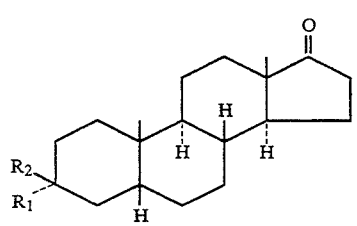
3α-Hydroxyetiocholan-17-
one ($R_1$ = OH, $R_2$ = H)
3β-Hydroxyetiocholan-17-
one ($R_1$ = H, $R_2$ = OH)
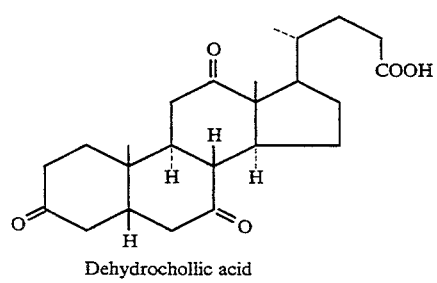
Dehydrochollic acid
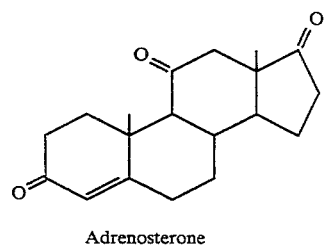
Adrenosterone
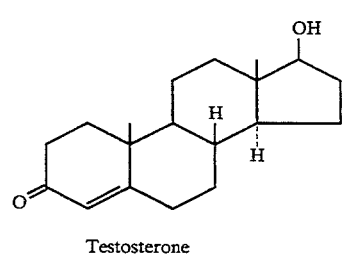
Testosterone
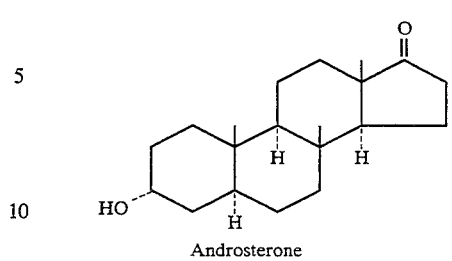
Androsterone
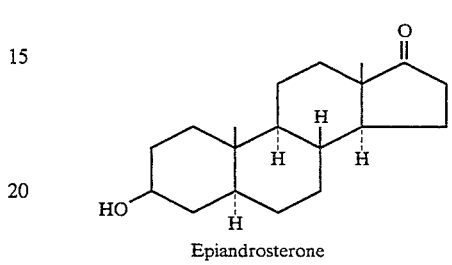
Epiandrosterone
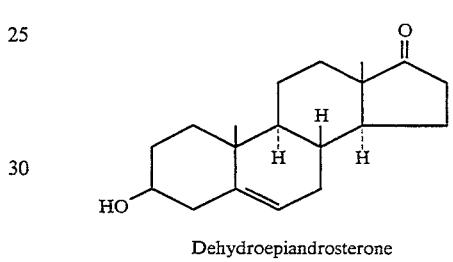
Dehydroepiandrosterone
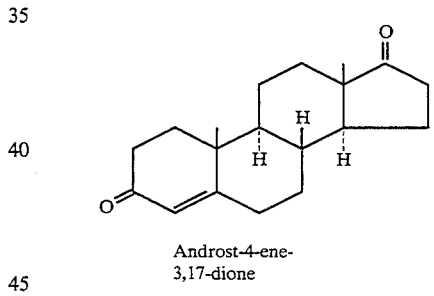
Androst-4-ene-
3,17-dione
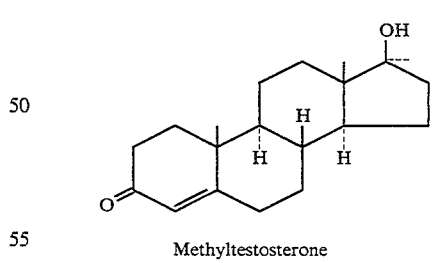
Methyltestosterone
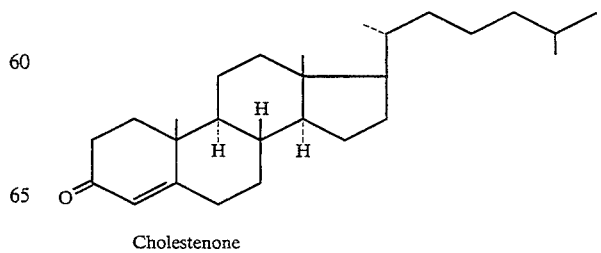
Cholestenone

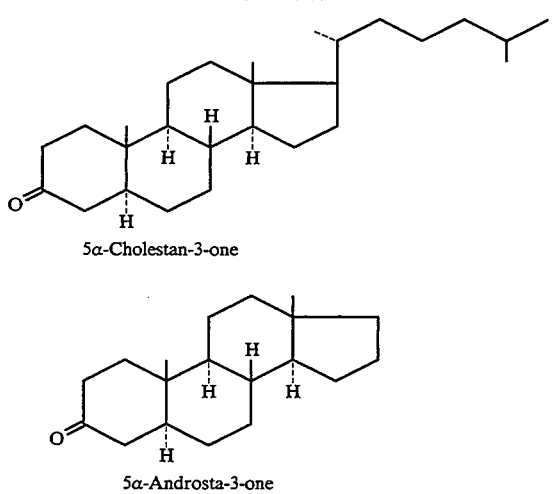

5α-Cholestan-3-one

5α-Androsta-3-one

As examples of substituted or unsubstituted aromatic aldehydes or heterocyclic aromatic aldehydes, mention may be made of benzaldehyde, 1-naphthaldehyde, 2-naphthaldehyde, 9-anthraldehyde, 4-chlorobenzaldehyde, 4-bromobenzaldehyde, 4-fluorobenzaldehyde, 4-cyanobenzaldehyde, 4-methoxybenzaldehyde, 4-methylthiobenzaldehyde, 4-aminobenzaldehyde, 4-methylaminobenzaldehyde, 4-dimethylaminobenzaldehyde, 4-ethylaminobenzaldehyde, 4-diethylaminobenzaldehyde, 4-dimethylamino-o-tolualdehyde, piperonal, vanillin, o-vanillin, p-tolualdehyde, 3,4-dimethoxybenzaldehyde, 2,3,4trimethoxybenzaldehyde, 3,4,5-trimethoxybenzaldehyde, 3-chlorobenzaldehyde, 3-bromobenzaldehyde, 3-fluorobenzaldehyde, 3-methoxybenzaldehyde, 3methylthiobenzaldehyde, 3-aminobenzaldehyde, 3-methylaminobenzaldehyde, 3-dimethylaminobenzaldehyde, 2-methoxybenzaldehyde, 2-thiophene aidehyde, 3-thiophene aidehyde, 2-pyridine aidehyde, nicotinic aidehyde, isonicotinic aidehyde, N-ethylcarbazole-3-aldehyde, indole-3aidehyde, etc.

In the present invention, it is preferable to react 4-diethylaminobenzaldehyde with 5-α-cholestan-3-one.

The steroidal ketone compound of the present invention may be obtained, for example, by using an equal mol to excessive mol of the aromatic aldehyde or heterocyclic aromatic aldehyde relative to the steroidal ketone compound having an active methylene group (a molar ratio of the steroid compound to the aldehyde in the range of 1.0 to 1.8 being preferable), and condensing the reactants in a solvent amounting from equivalent weight to about 20 times the total weight of the steroidal ketone compound and the aldehyde in the presence of a catalyst and optionally with heating. Examples of preferred solvents include methanol, ethanol, 2-butanol, methyl Cellosolve, ethyl Cellosolve, tetrahydrofuran and dioxane. Examples of preferred catalysts include sodium hydroxide, potassium hydroxide, lithium hydroxide, barium hydroxide, tetramethylammonium hydroxide, piperidine, morpholine, sodium ethoxide and sodium methoxide. The catalyst is used in an amount of 1–5% by weight based on the weight of the steroidal ketone compound. The reaction temperature is generally from room temperature to 150° C.

The non-linear optical material according to the present invention may be obtained either by using the steroidal ketone compound mentioned above or by using a composition prepared by dissolving or dispersing the compound in a high molecular compound. Examples of high molecular compounds which may be used include homopolymers or copolymers of such monomers as methyl acrylate, methyl methacrylate, ethyl acrylate, ethyl methacrylate, n-butyl acrylate, n-butyl methacrylate, cyclohexyl acrylate, cyclohexyl methacrylate, acrylic acid, methacrylic acid, styrene, itaconic acid, maleic anhydride, vinyltoluene, divinylbenzene, vinyl chloride, β-hydroxyethyl acrylate, β-hydroxyethyl methacrylate, glycidyl acrylate and glycidyl methacrylate, polyester, polyamide, polyurethane, polycarbonate, cellulose ester, polyether, etc.

The composition mentioned above may be prepared by mixing and dissolving the steroidal ketone compound and a monomer corresponding thereto and then polymerizing the mixture with the action of light or heat, or it may be obtained by dissolving and mixing the high molecular compound mentioned above and the steroidal ketone compound through the use of a suitable solvent, followed by removal of the solvent. The non-linear optical property of the composition can be improved by performing poling during polymerization in the former method, or by performing poling after obtaining the composition both in the former method and in the latter method.

The non-linear optical material of the present invention can be used in the form of bulk crystal individually or as a part of a waveguide type optical device of fiber type, slab type, plane type, channel type, etc. Examples of the non-linear optical devices using said non-linear optical material include wavelength conversion devices which make use of second harmonic generation, sum frequency wave generation or optical parametric oscillation, and phase modulation devices and polarization plane modulation devices which make use of an electro-optical effect.

The steroidal ketone compound of the present invention has a $\pi$ electron system which further increases its polarity in excited states. Moreover, the molecules of the compound have a rigid and bulky steric regulating group, so that they are, in aggregated states, apt to assume a structure of noncentrosymmetric, and hence the compound does not lose its lowest order non-linear optical effects such as second harmonic generation, Pockels effect, etc.

The present invention will be described in detail below with reference to Examples.

EXAMPLE 1

Synthesis of steroidal ketone compound 1

In a 50-ml pear shaped flask were placed 1.33 g of 5α-cholestan-3-one and 600 mg of 4-diethylaminobenzaldehyde, then 10 ml of methanol and 2 ml of an aqueous 40% sodium hydroxide solution were added thereto, and the mixture was heated under reflux for 24 hours while stirring with a magnetic stirrer. The reaction mixture was poured into an ice-water mixture, upon which pale yellow powdery crystals separated out. The crystals were collected by filtration under suction and dried under vacuum in a desicator. The yield was 1.23 g (about 64%). The crude crystals thus obtained were purified by recrystallization from acetone. M.p. : 151.3°C.

Figure 3:
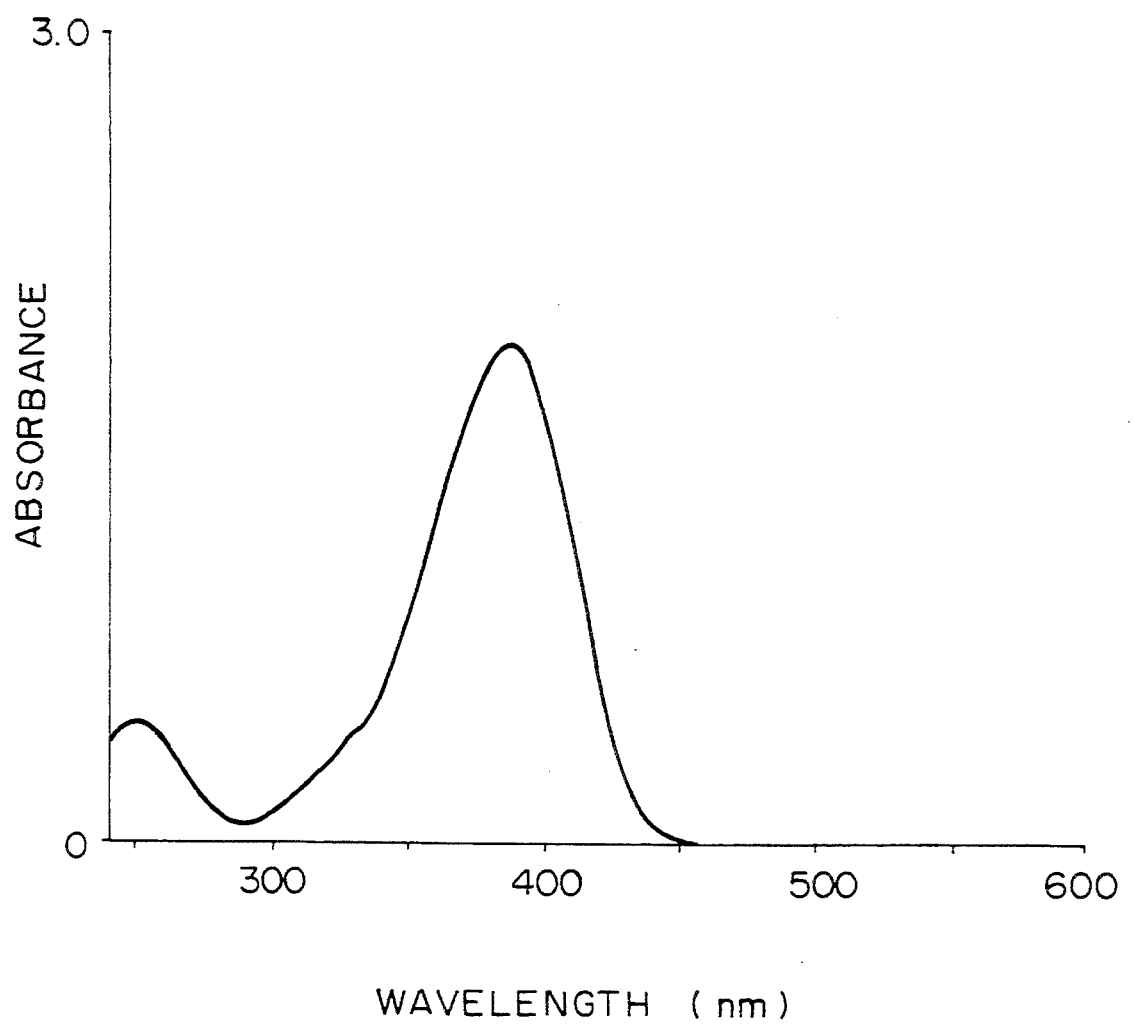
FIG. 3 shows UV-VIS (ultraviolet-visible region absorption) spectrum of the steroidal ketone compound obtained in Example 1.
Figure 4:
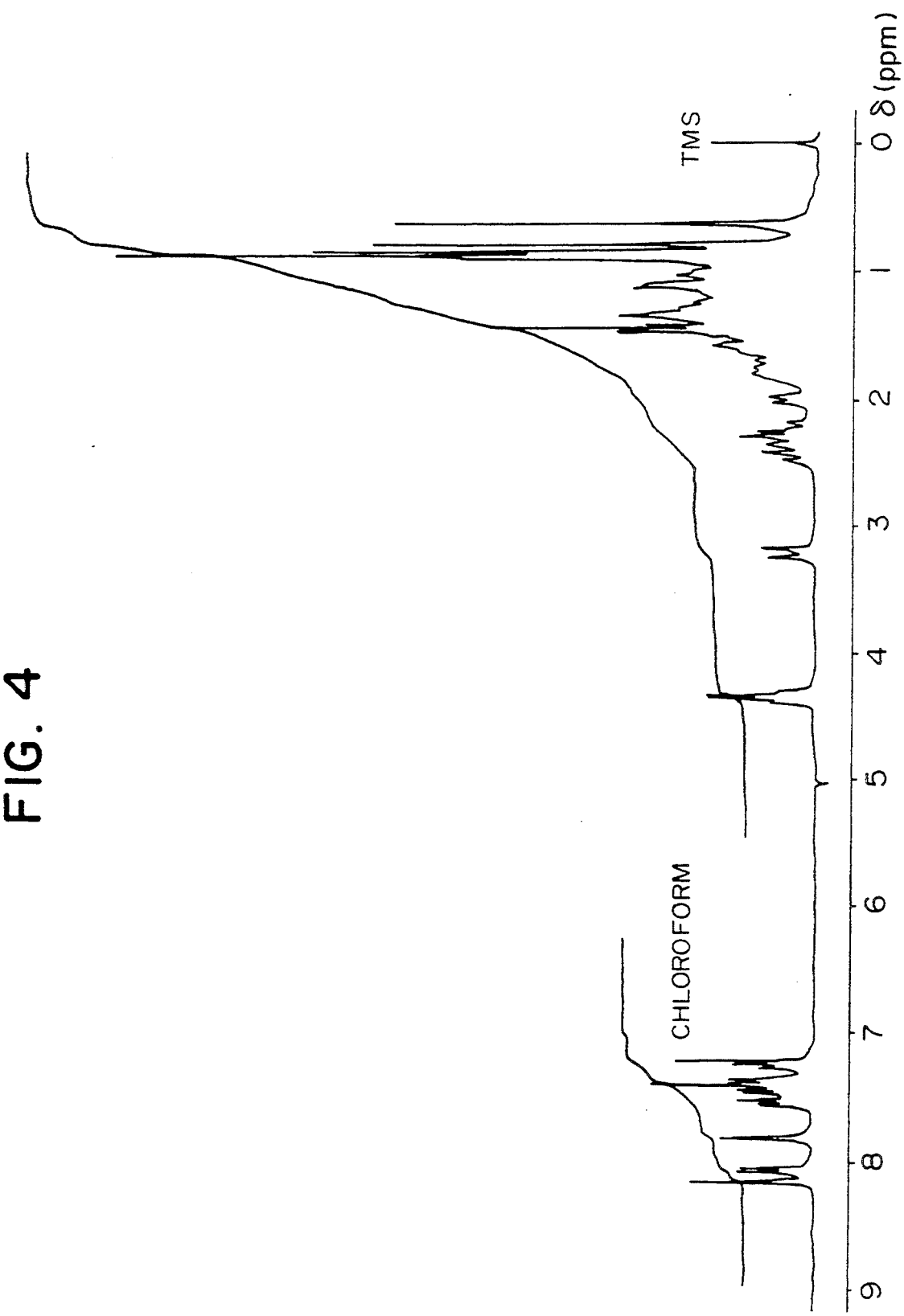
FIGS. 4–10 show the NMR charts of the steroidal ketone compounds 2–8 obtained in Examples 3–9.
Figure 5:
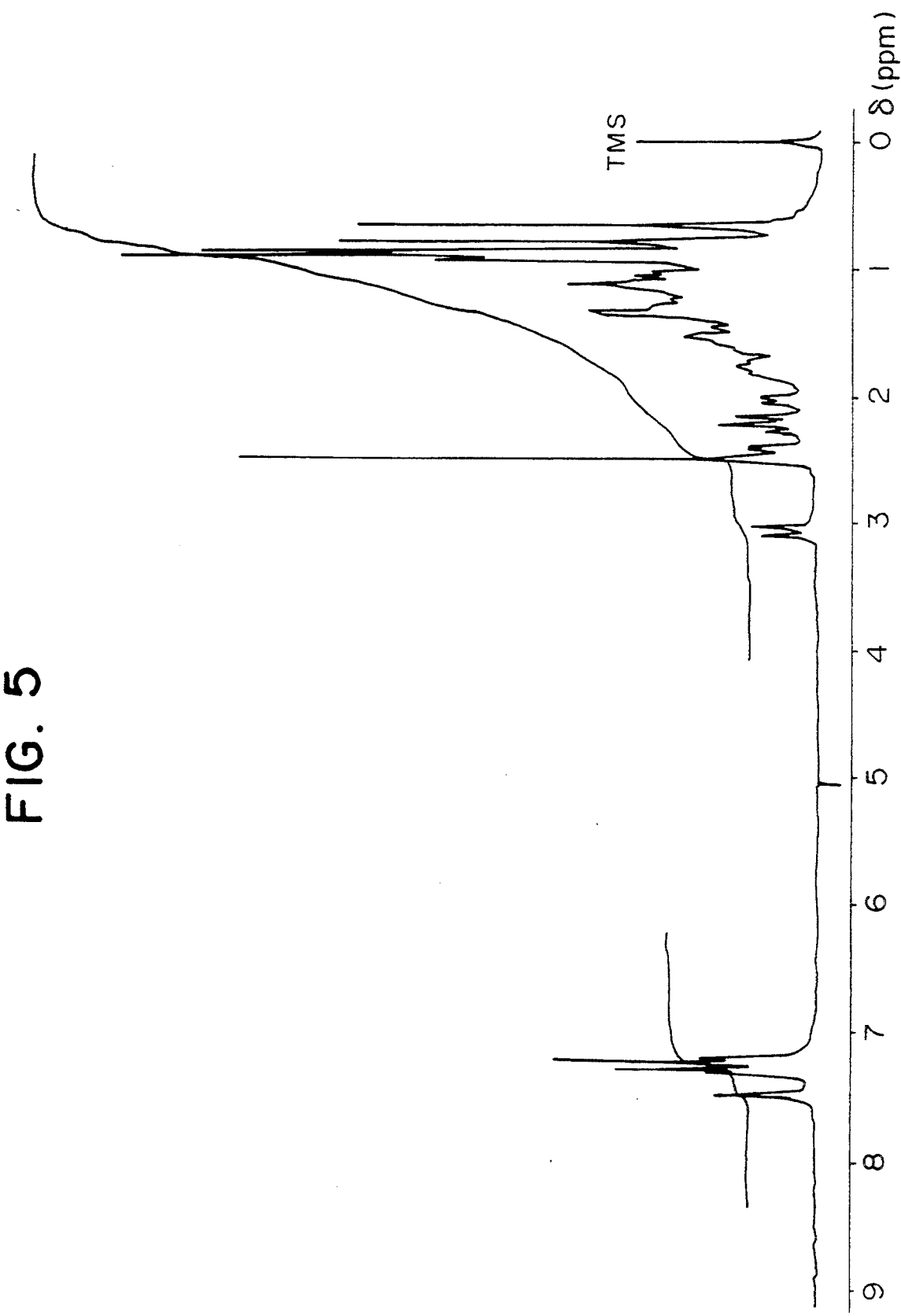
Figure 6:
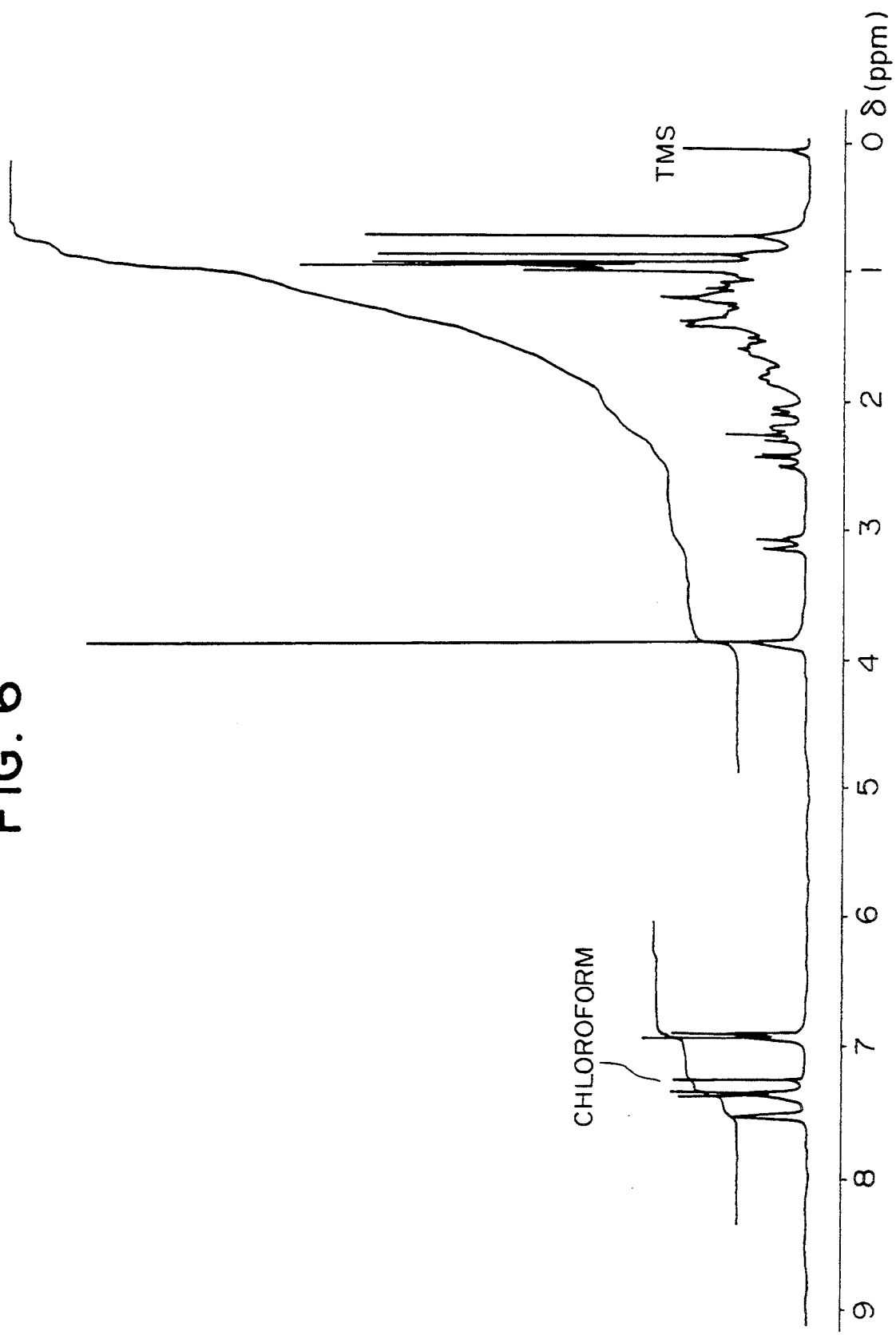
Figure 7:
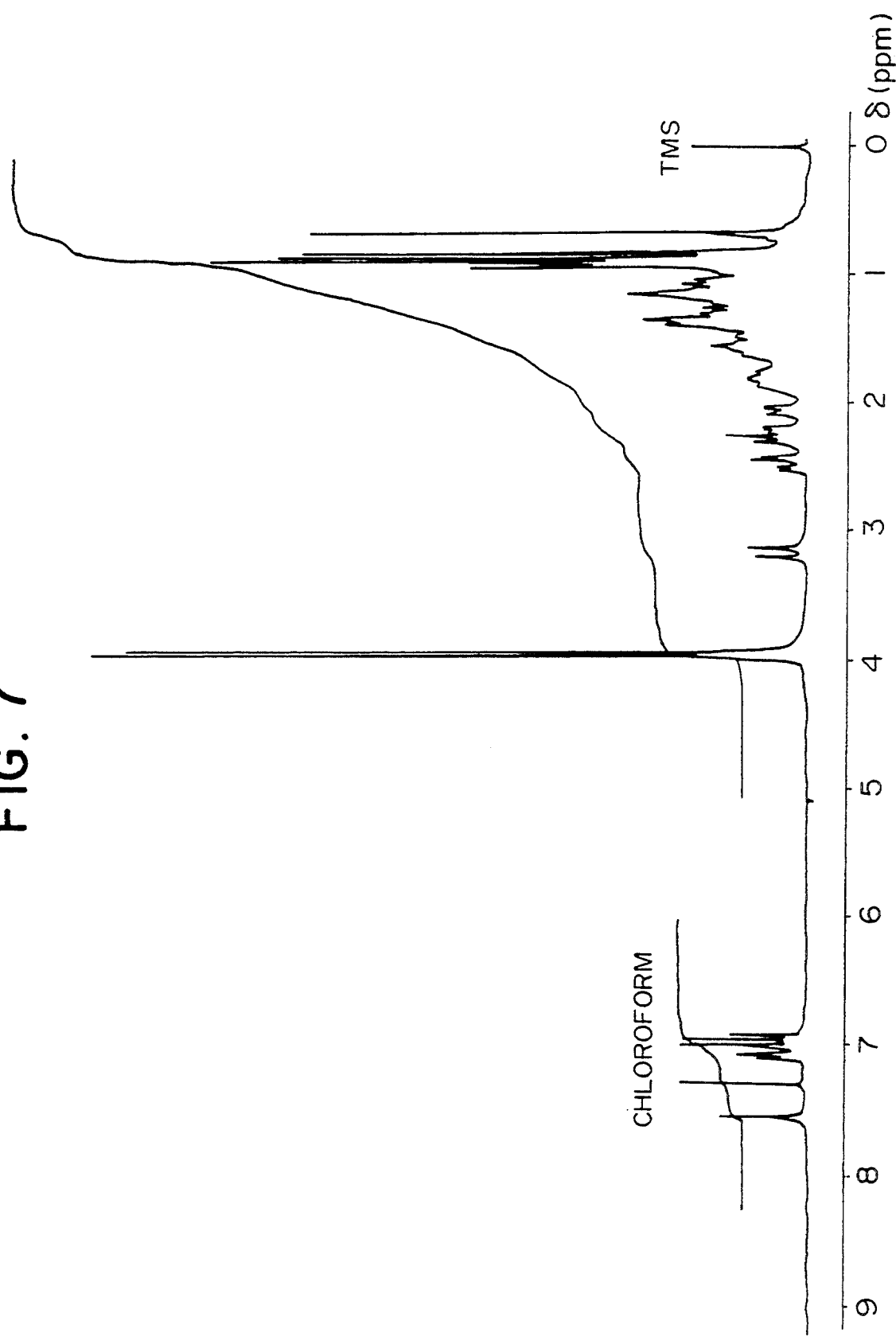
Figure 8:
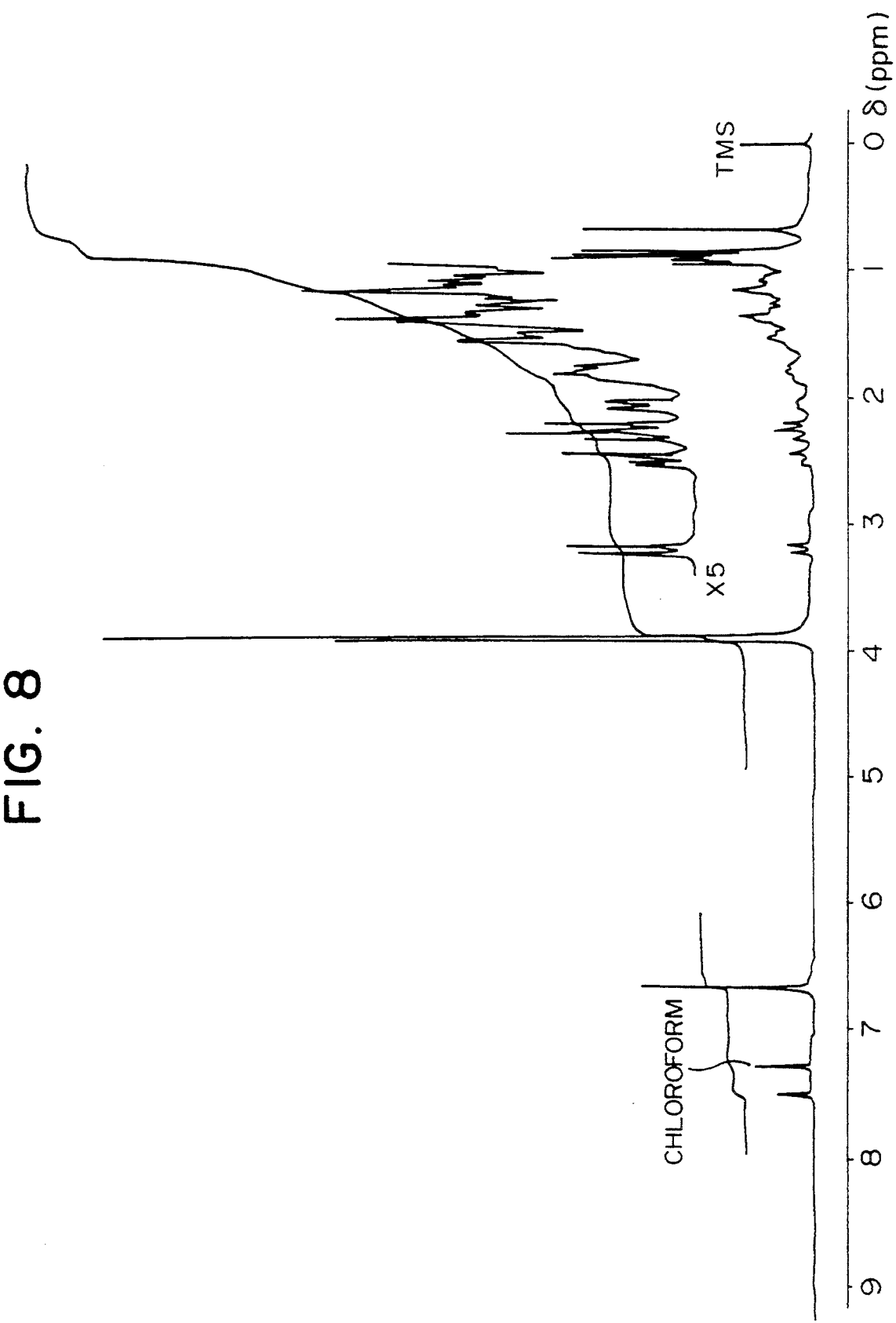
Figure 9:
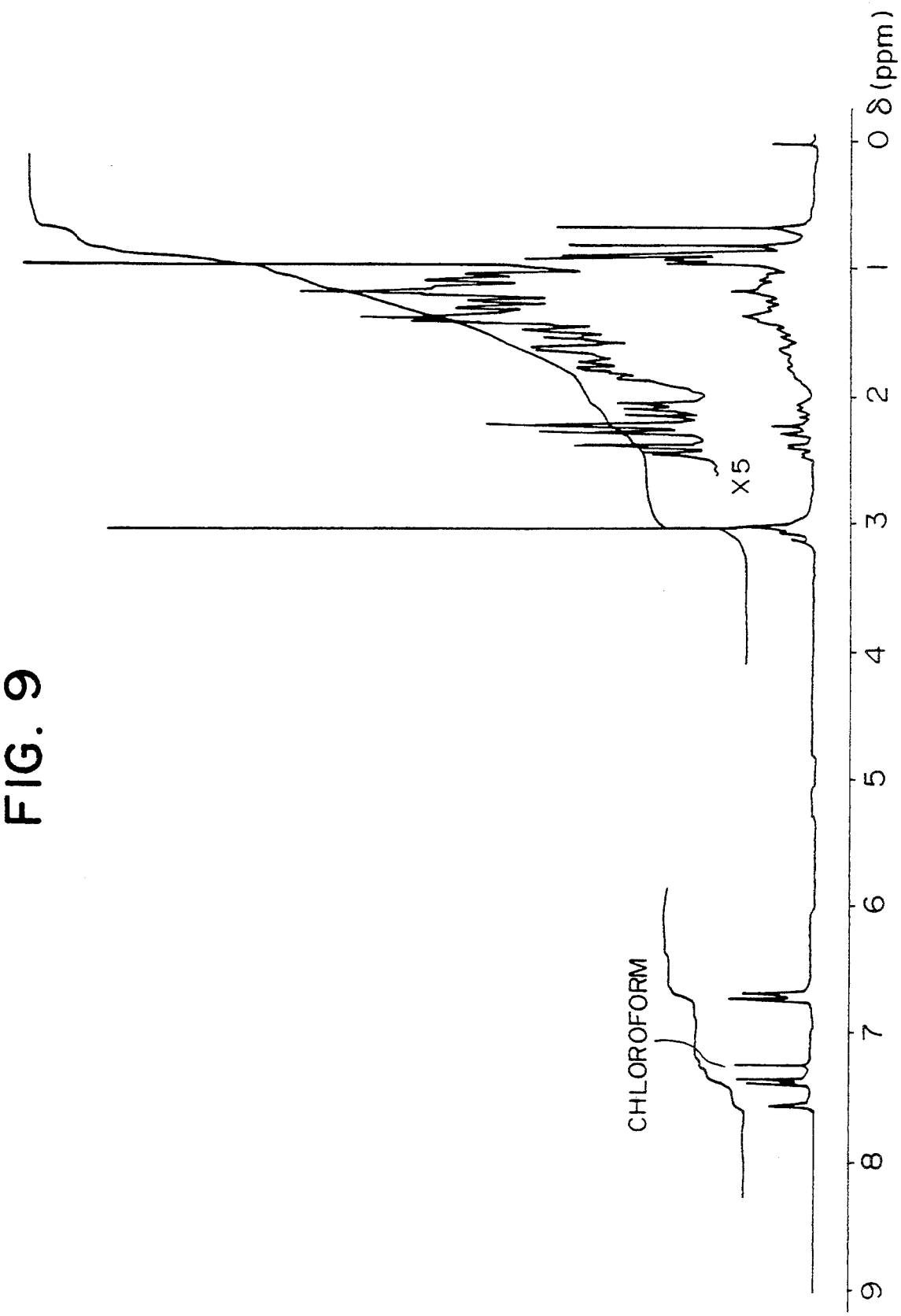
Figure 10:
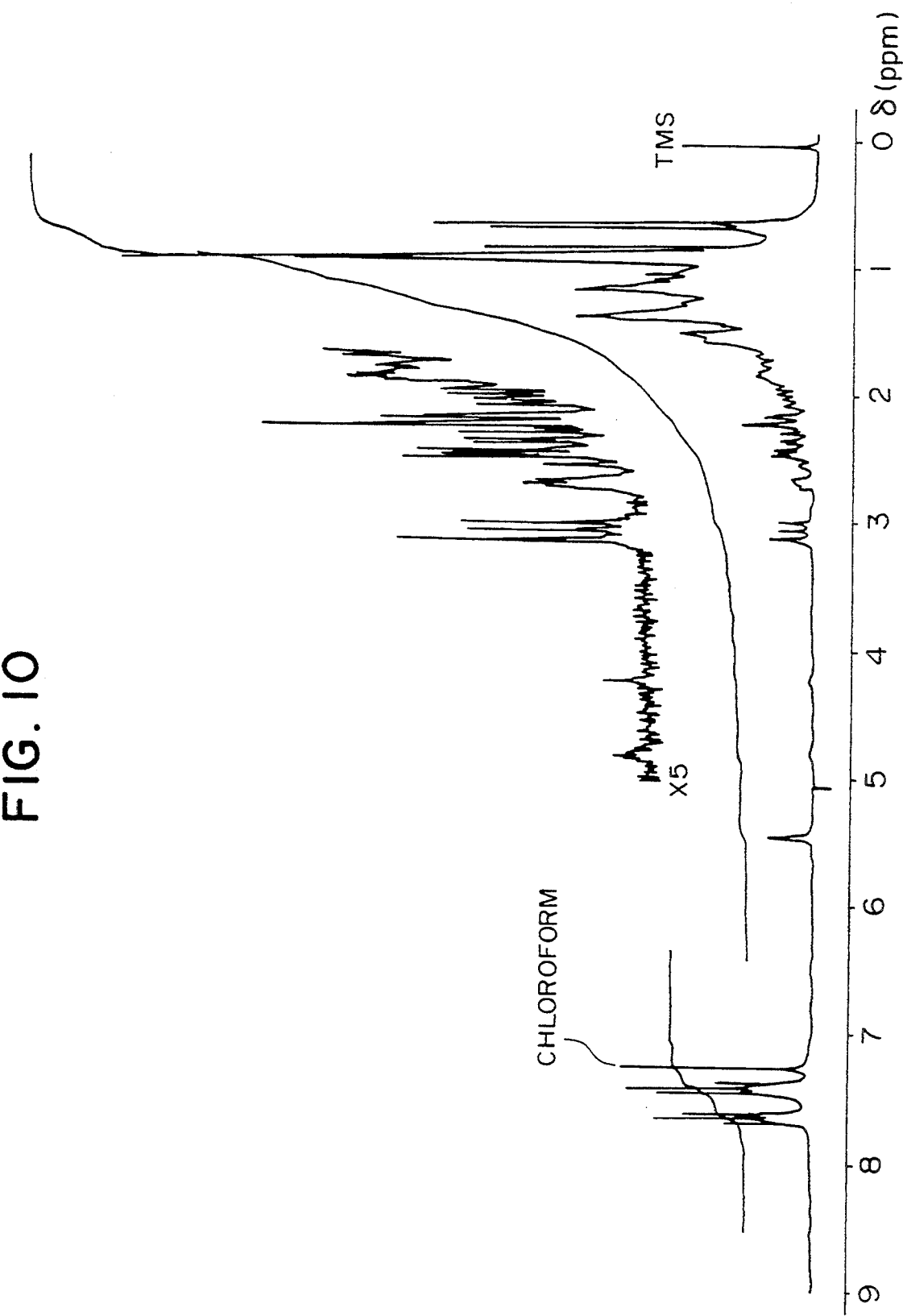
Figure 11:
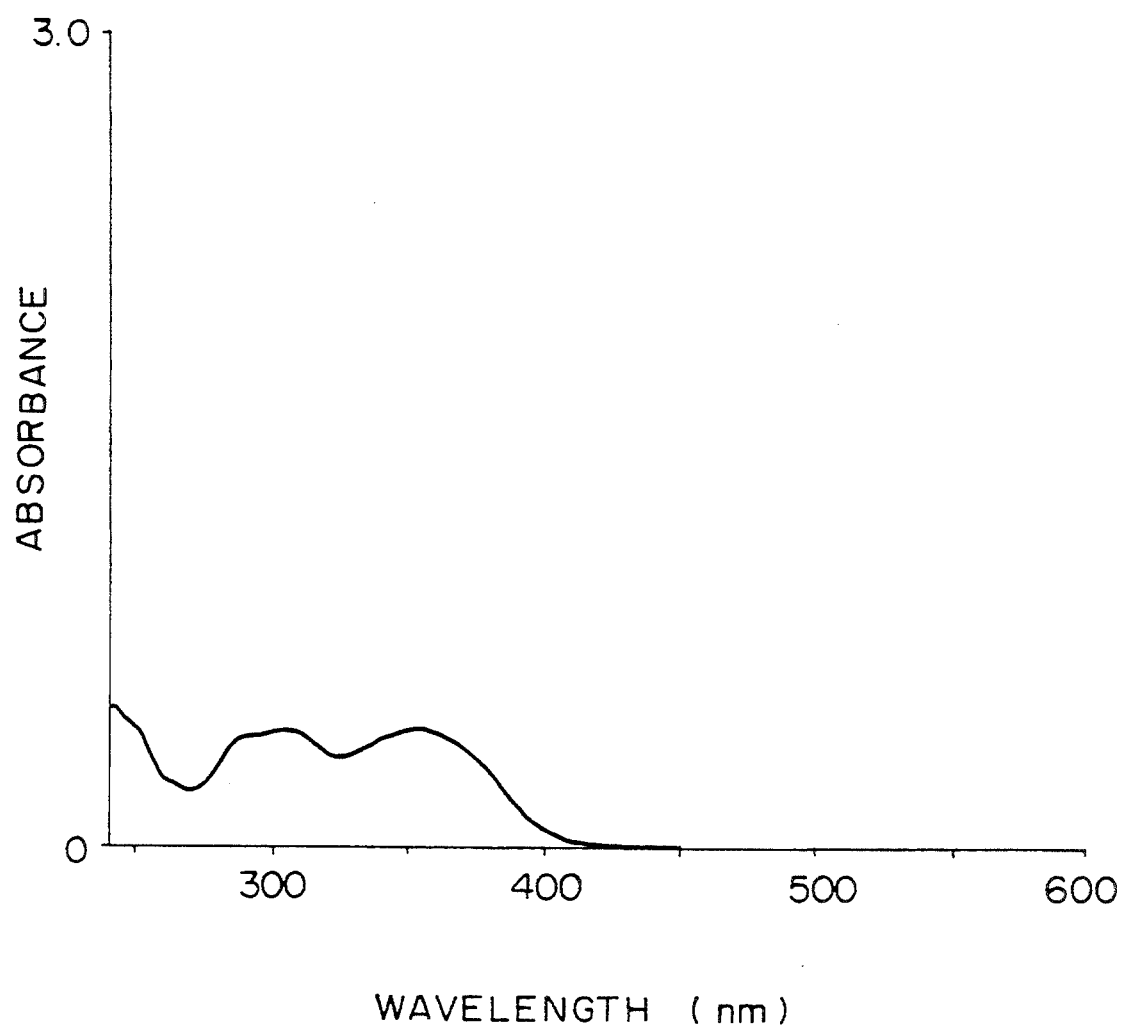
FIGS. 11–17 show the UV-VIS spectra of these compounds.
Figure 12:
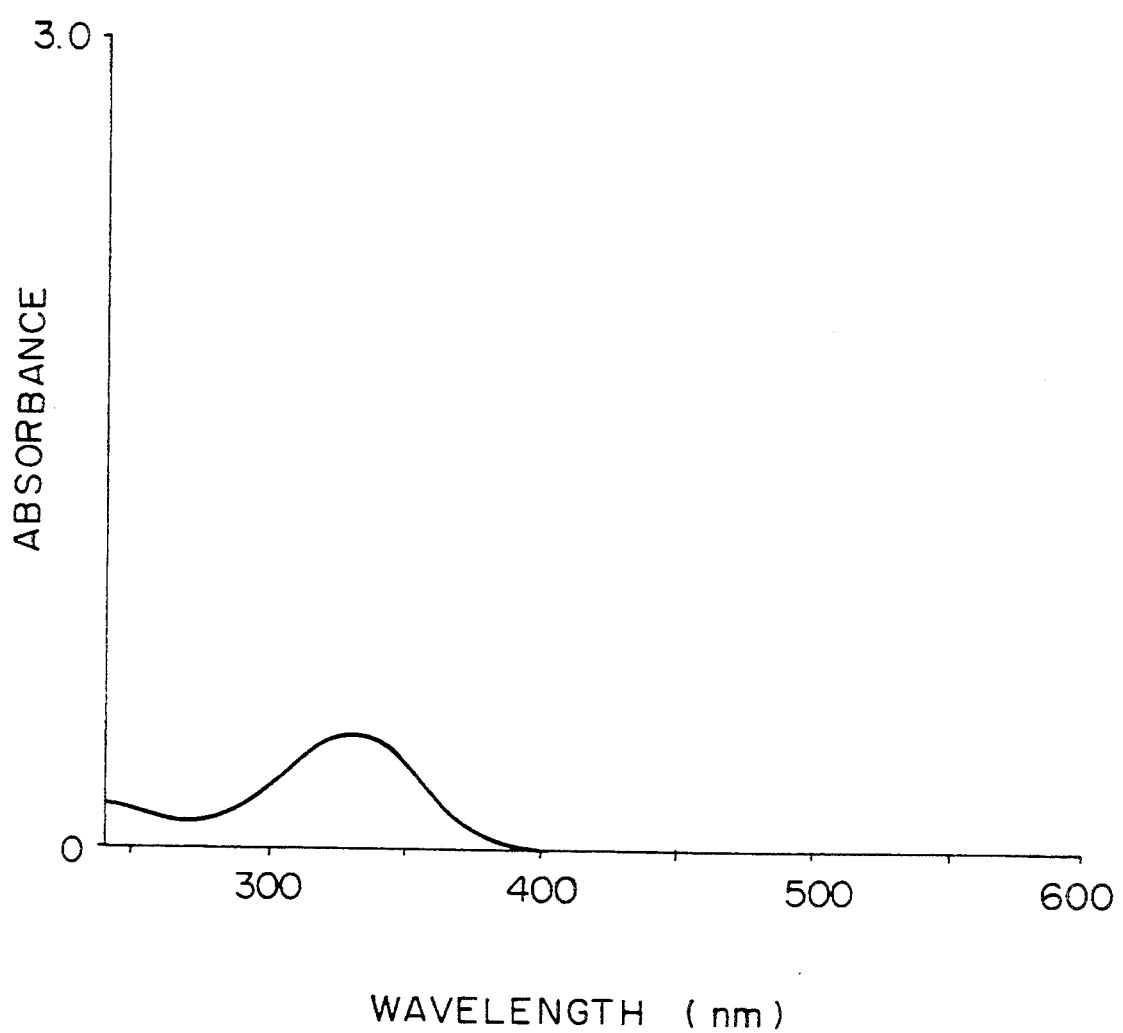
Figure 13:
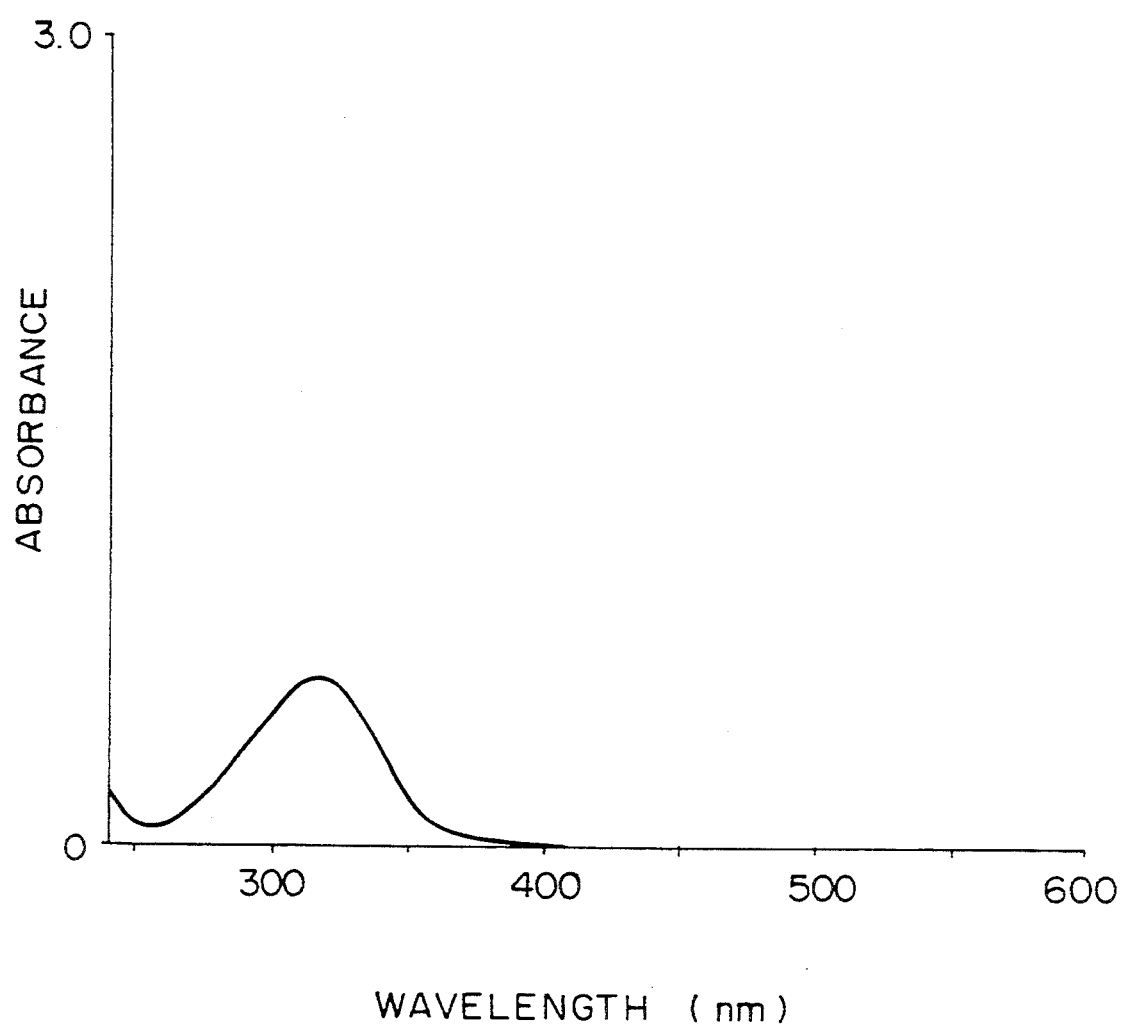
Figure 14:
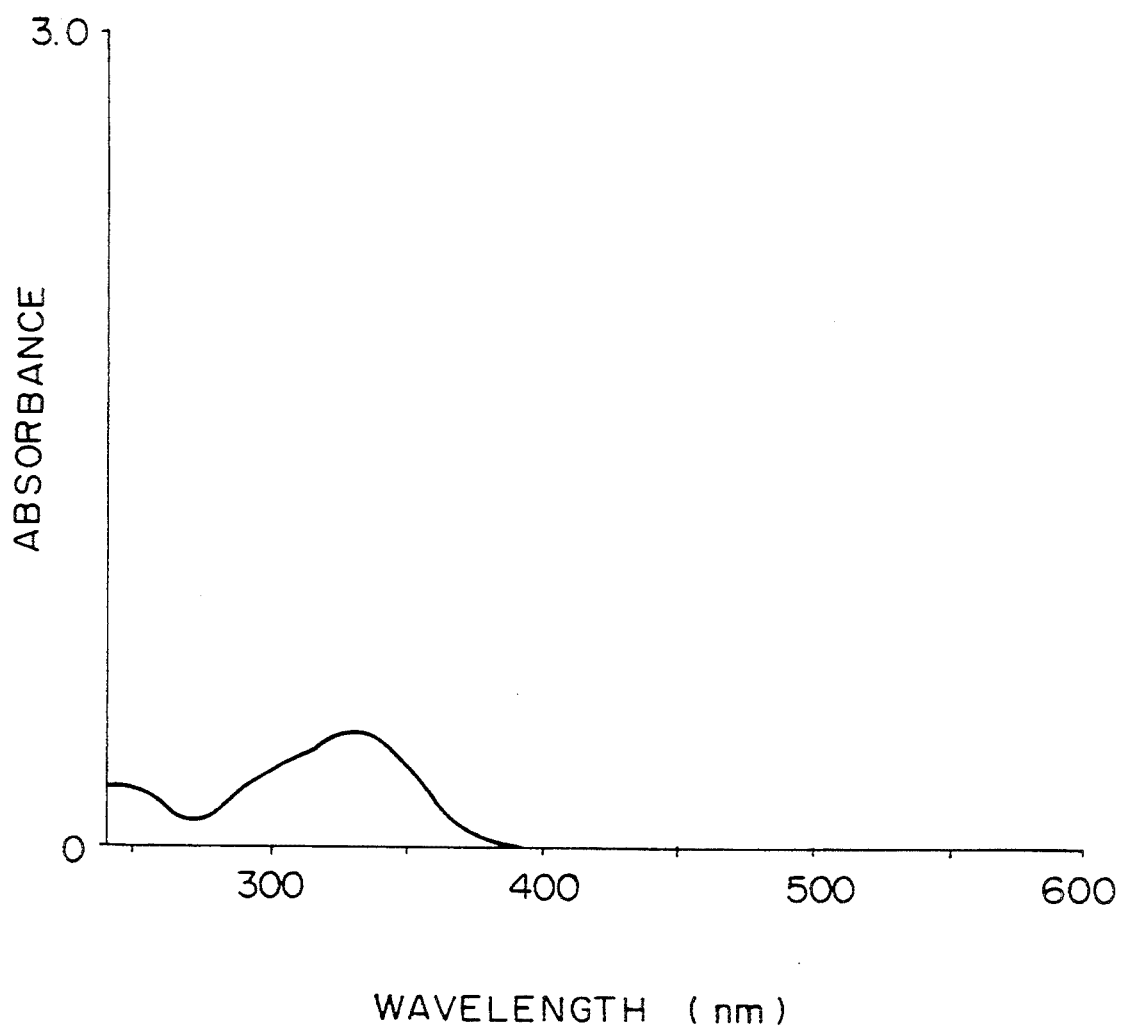
Figure 15:
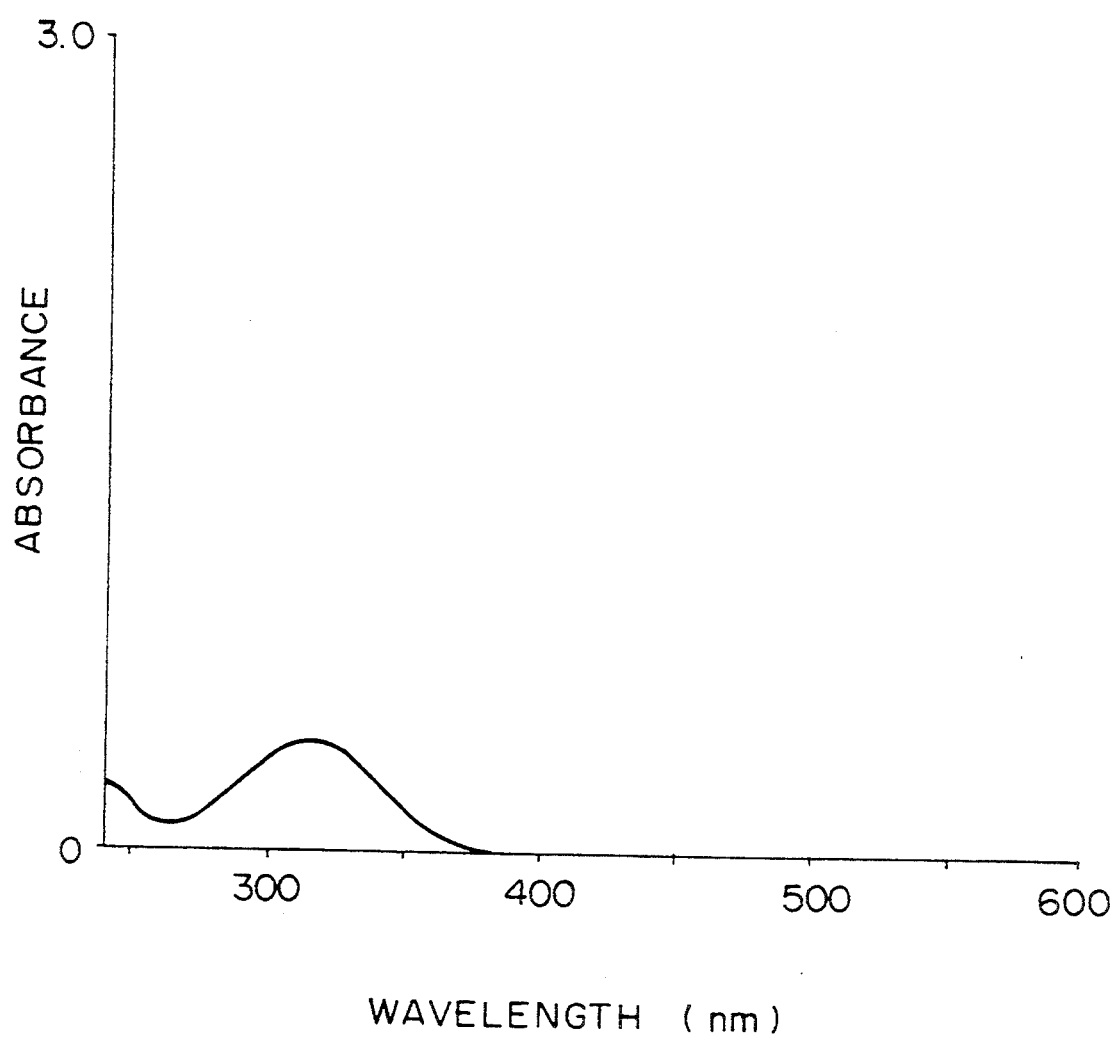
Figure 16:
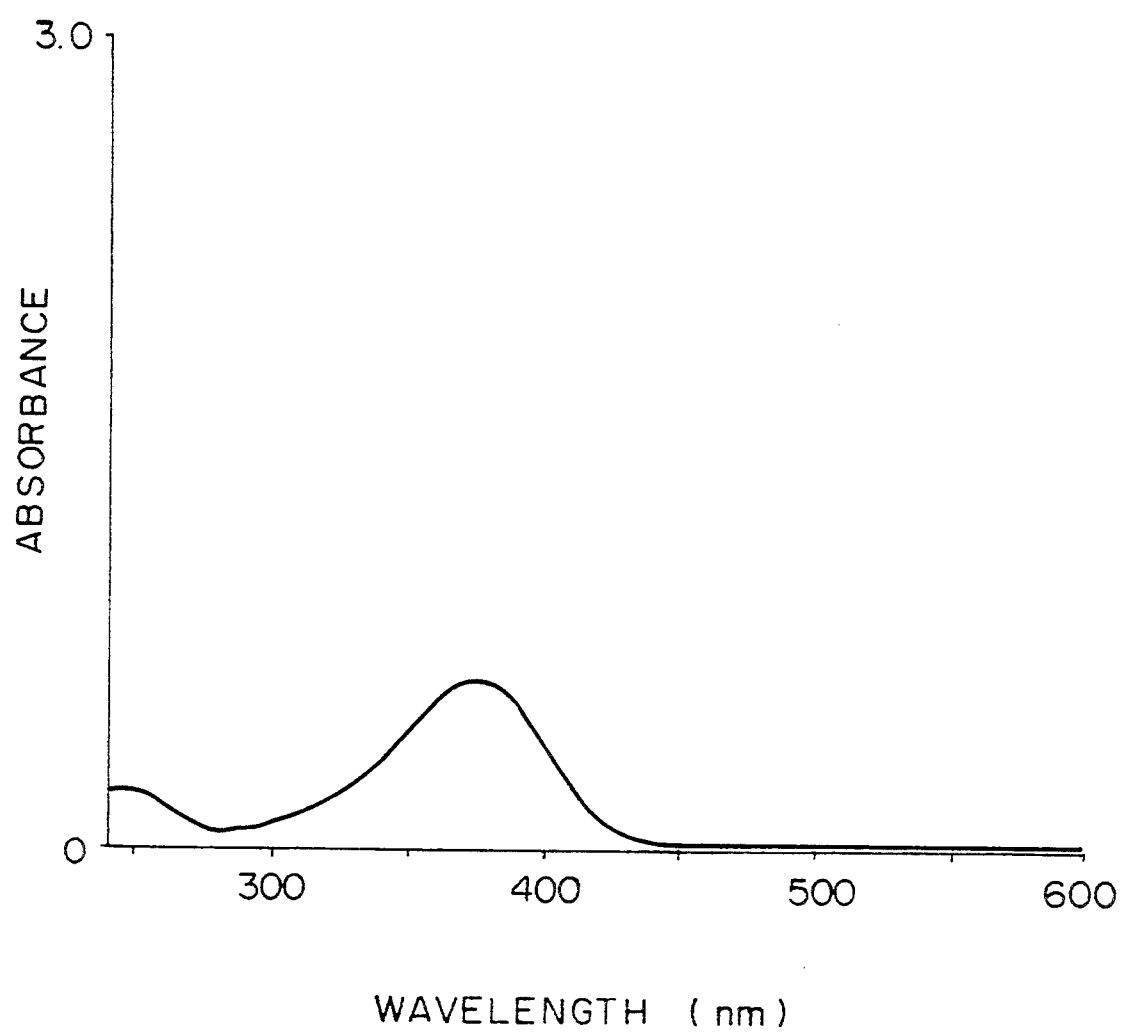
Figure 17:
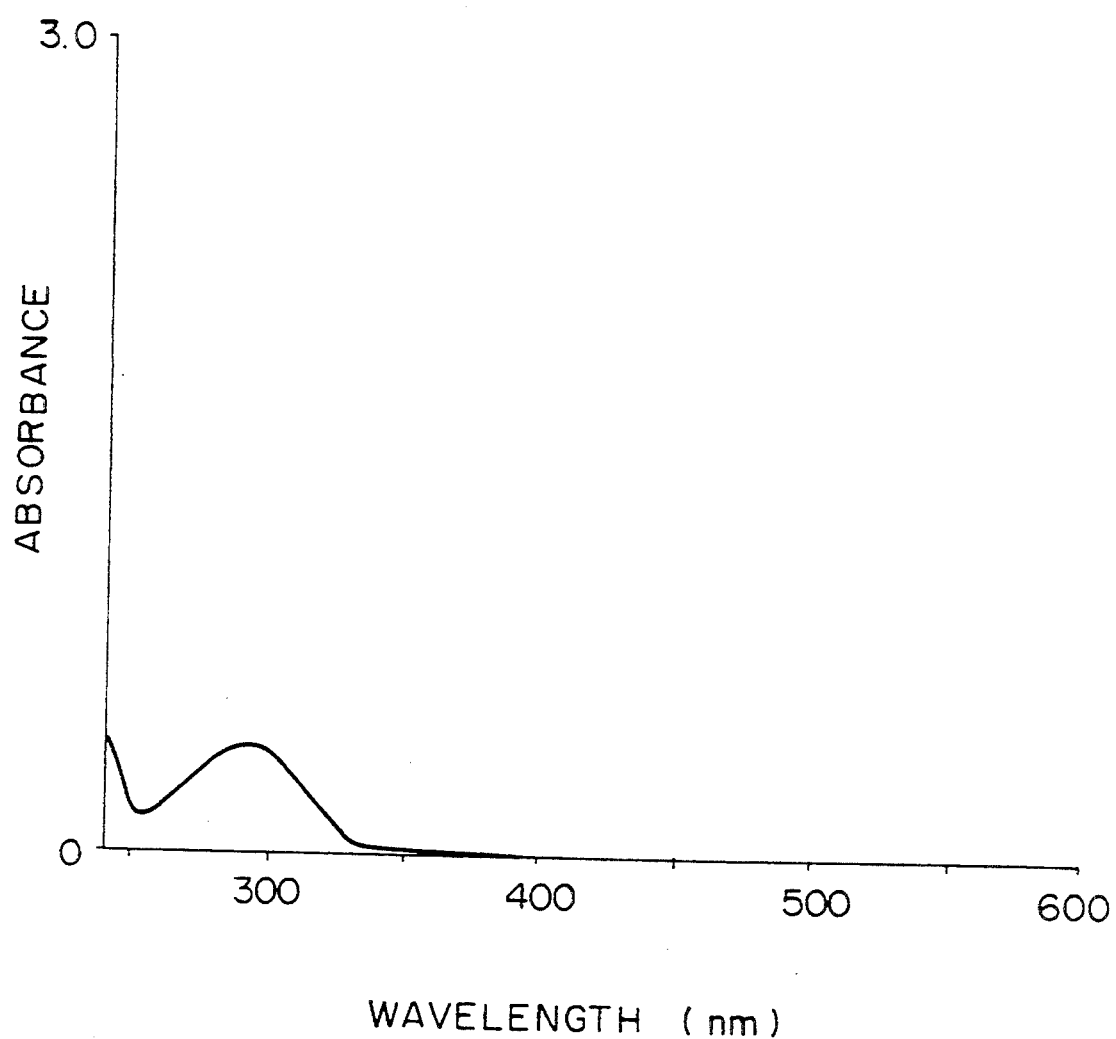

FIG. 1 shows the NMR chart of the compound thus obtained (250 MHz, solvent used for measurement: deutero chloroform, interval standard used: tetramethylsilane (TMS)). FIG. 3 shows UV-VIS spectrum of the compound in methylene chloride. The absorption maximum wavelength was 387.2 nm.

The compound is estimated to have the following structure.

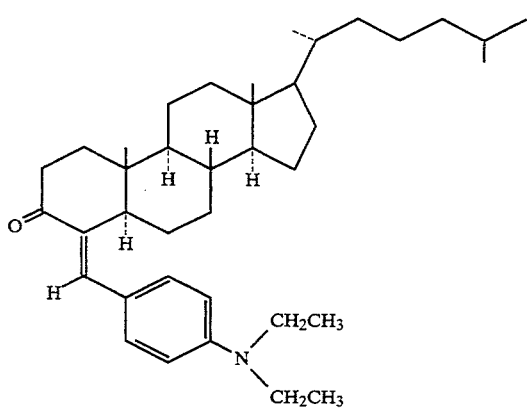

EXAMPLE 2

The steroidal ketone compound 1 synthesized in Example 1 was ground thoroughly in a mortar, and particles of a diameter of 100 μm to 125 μm were collected by use of sieves. The particles thus collected were examined for the second harmonic generation efficiency by means of the powder method using a Pulse Nd: YAG Laser (Type SL303, mfd. by Spectrolaser System Corp., output: 850 mJ, half value width: 15 ns, output per pulse: 50 MW, beam diameter : 9.5 mm, wave length: 1.064 μm). The intensity of the second harmonic generated was examined by separating the light of 532 nm with a monochromator and by using a photo-multiplier. The intensity was found to be about 0.8 time that of MNA (4-nitro-2-methylaniline), a known material.

Figure 2A:
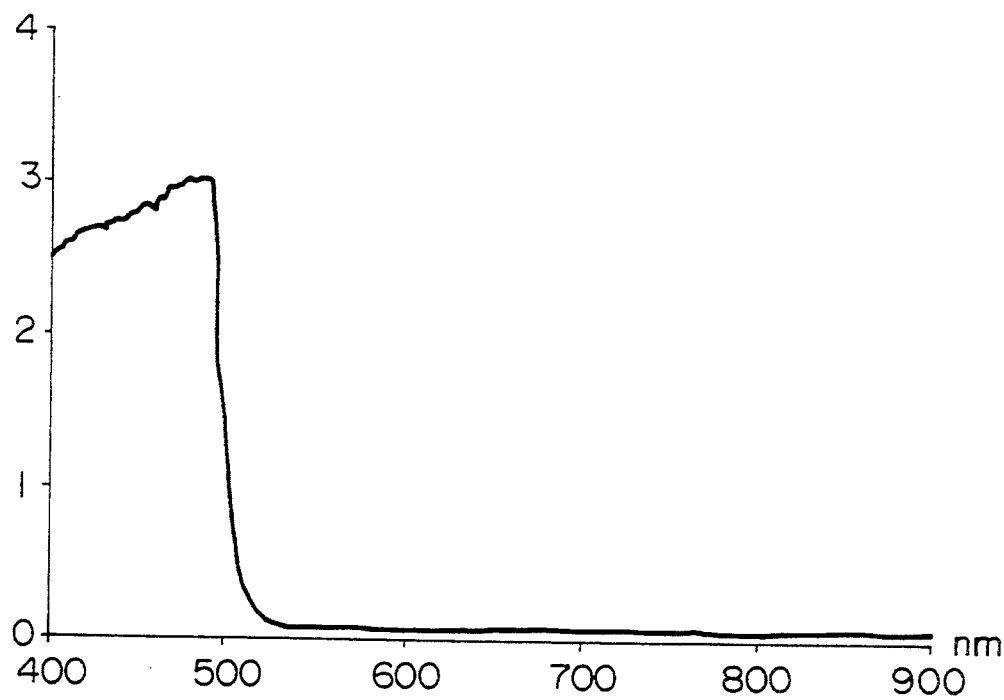
FIG. 2(a) shows the absorption spectrum of MNA.
Figure 2B:
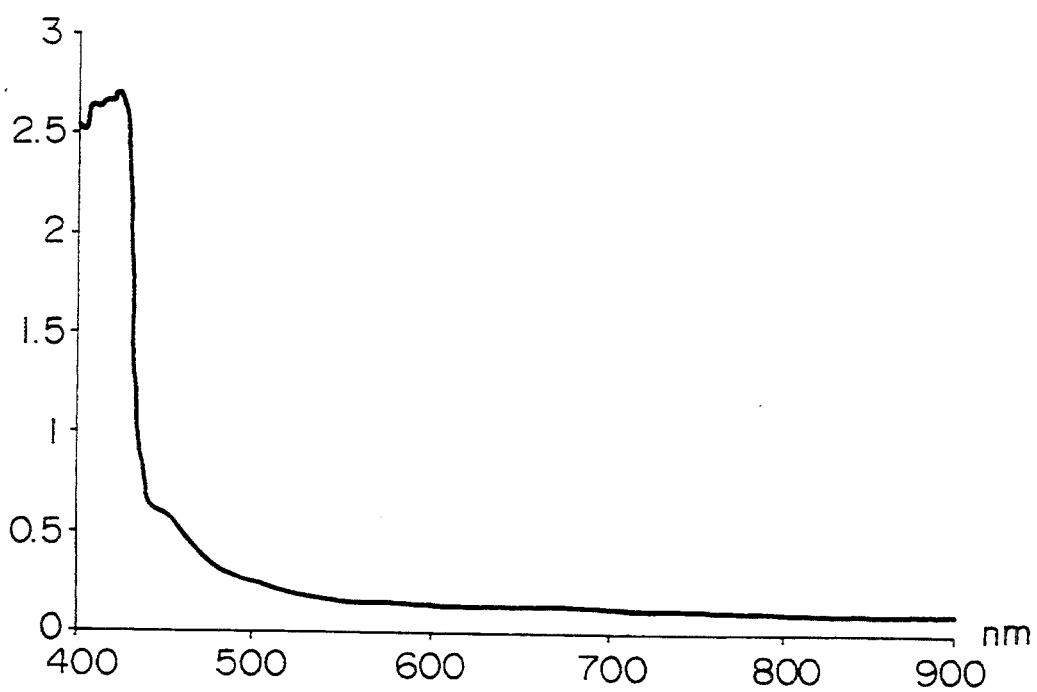
FIG. 2(b) shows the absorption spectrum of the steroidal ketone compound 1.

The absorption spectrum of the crystal of the compound is shown in FIG. 2 in comparison with that of MNA. In FIG. 2, (a) refers to the absorption spectrum of MNA and (b) refers to that of the steroidal ketone compound 1. It is recognized that the α-benzylidenesteroid ketone compound 1 has a more excellent transparency in the visible region and the same second harmonic generation efficiency as compared with MNA.

EXAMPLES 3–9

4-Diethylaminobenzaldehyde, 600 mg, used in Example 1 was replaced respectively with 756 mg of N-ethyl-carbazole-3-aldehyde, 515 mg of 4-methylthiobenzaldehyde, 461 mg of 4-methoxybenzaldehyde, 563 mg of 3,4-dimethoxybenzaldehyde, 664 mg of 3,4,5-trimethoxybenzaldehyde, 505 mg of 4-dimethylaminobenzaldehyde and 444 mg of 4-cyanobenzaldehyde and reacted in the same manner as in Example 1 with 1.33 g of 5α-cholestan-3-one in methanol with sodium hydroxide used as the catalyst under reflux with heating. The reaction product was allowed to cool to form crystals. The crystals were collected by filtration under suction, washed thoroughly with cold methanol and dried under vacuum in a desicator. The resulting crude crystals were purified by recrystallization from acetone (the resulting products are respectively termed Compounds 2, 3, 4, 5, 6, 7 and 8). The melting points and UV-VIS absorption maximum wavelengths of these compounds thus obtained are shown in Table 1. Further, the respective NMR charts (250 MHz, solvent used in measurement: deutero chloroform, interval standard used: TMS) of the Compounds 2, 3, 4, 5, 6, 7 and 8 are shown in FIGS. 4, 5, 6, 7, 8, 9 and 10. Further, the respective UV-VIS spectra of the Compounds 2, 3, 4, 5, 6, 7 and 8 determined in methylene chloride solutions are shown in FIGS. 11, 12, 13, 14, 15, 16 and 17.

TABLE 1

| Example No. | Steroidal ketone compound | $R_1$ the estimated structural formula shown below | Melting point (°C.) | λmax (nm) |
| --- | --- | --- | --- | --- |
| 3 | Compound 2 | carbazole-N-Et | 197.8 | 353.0 |
| | Compound 3 | C₆H₄–SMe | 150.3 | 331.2 |
| 5 | Compound 4 | C₆H₄–OMe | 159.6 | 316.8 |
| 6 | Compound 5 | C₆H₃(OMe)₂ | 143.7 | 320.9 |

TABLE 1-continued

| Example No. | Steroidal ketone compound | R₁ the estimated structural formula shown below | Melting point (°C.) | λmax (nm) |
|---|---|---|---|---|
| 7 | Compound 6 | 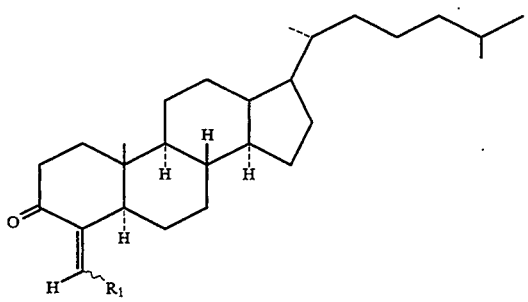 | 145.1 | 318.1 |
| 8 | Compound 7 | 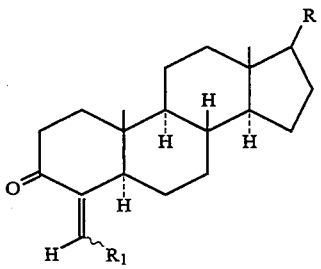 | 176.0 | 376.0 |
| 9 | Compound 8 | 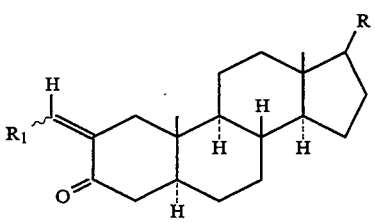 | 192.3 | 293.1 |

Note:
Et denotes the ethyl group and Me the methyl group.

EXAMPLES 10–16

The second harmonic generation (SHG) efficiencies of the Compounds 2, 3,.4, 5, 6, 7 and 8 were determined according to the same method as in Example 2, except that urea was used as the control sample in place of MNA. The results are shown in Table 2.

TABLE 2

| Example No. | Compound | SHG efficiency |
|---|---|---|
| 10 | 2 | 11 |
| 11 | 3 | 4 |
| 12 | 4 | 2.6 |
| 13 | 5 | 5 |
| 14 | 6 | 3.6 |
| 15 | 7 | 14 |
| 16 | 8 | 0.2 |
| Comparative Example | Urea | 1 |

The steroidal ketone compound of the present invention has an outstanding non-linear optical property and an excellent transparency in the visible region which is required for wavelength conversion materials and hence can provide a non-linear optical material and a non-linear optical device which have a high non-linear optical coefficient.

What is claimed is:

1. A steroidal ketone compound represented by the formula:

or the formula:

wherein R is an alkyl group having 1–20 carbon atoms; the bond shown by ∼ denotes a cis- or a trans-position; and R₁ is a substituted heterocyclic aromatic group of the formula:

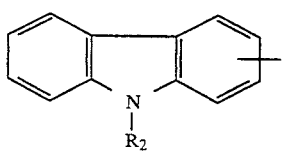

wherein $R_2$ is an alkyl group having 1 to 6 carbon atoms.

2. A steroidal ketone compound represented by the formula:

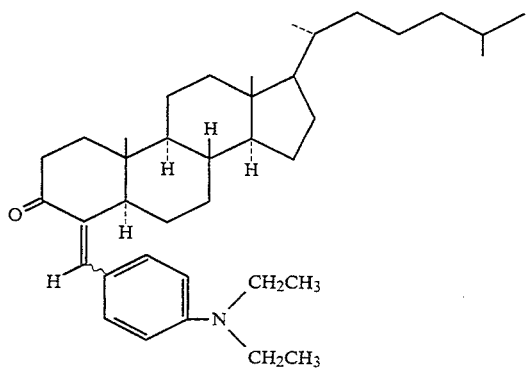

wherein R is an alkyl group having 1-20 carbon atoms; X is an amino group, an alkylamino group having 1 to 6 carbon atoms, a dialkylamino group having 1 to 6 carbon atoms in each alkyl group, an acylated amino group having 1 to 6 carbon atoms, a hydroxyl group, a thioal- kyl group having 1 to 6 carbon atoms, an alkyl group having 1-20 carbon atoms, a nitro group, a cyano group or a halogen atom, provided that when n is two or more these groups and atoms may be different from one another; the bond shown by ∼ denotes a cis- or trans-position; and n ms an integer of 1 to 5.

3. A steroidal ketone compound represented by the formula:

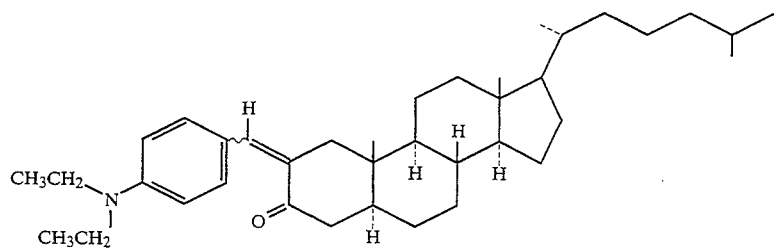

or the formula:

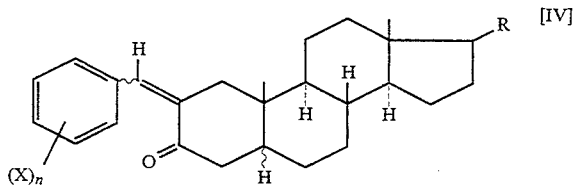

wherein the bond shown by ∼ denotes a cis- or trans-position.

4. A non-linear optical material comprising a steroidal ketone compound of claim 1.

5. A non-linear optical material comprising a steroidal ketone compound of claim 2.

6. A non-linear optical material comprising a steroidal ketone compound of claim 3.

7. A non-linear optical material comprising a composition containing a steroidal ketone compound of claim 1.

8. A non-linear optical material comprising a composition containing a steroidal ketone compound of claim 2.

9. A non-linear optical material comprising a composition containing a steroidal ketone compound of claim 3.

10. A non-linear optical device using the non-linear optical material of claim 4.

11. A non-linear optical device using a non-linear optical material comprising a steroidal ketone compound represented by the formula:

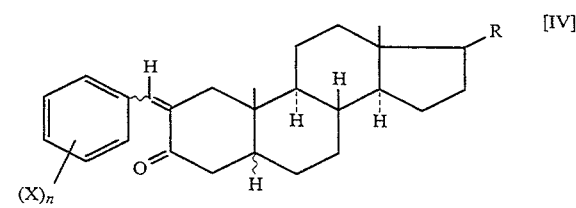

-continued or the formula:

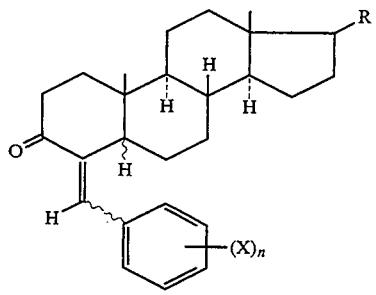

[V]

wherein R is an alkyl group having 1–20 carbon atoms; X is an amino group, an alkylamino group having 1 to 6 carbon atoms, a dialkylamino group having 1 to 6 carbon atoms in each alkyl group, an acylated amino group having 1 to 6 carbon atoms, a hydroxyl group, an alkoxy group having 1 to 6 carbon atoms, a thioalkyl group having 1 to 6 carbon atoms, an alkyl group having 1–20 carbon atoms, a nitro group, a cyano group or a halogen atom, provided that when n is two or more these groups and atoms may be different from one another; the bond shown by~denotes a cis- or trans-position; and n is an integer of 1 to 5.

12. A non-linear optical device using the non-linear optical material of claim 6.

13. A non-linear optical device using the non-linear optical material of claim 7.

14. A non-linear optical device using a non-linear optical material comprising a composition containing a steroidal ketone compound represented by the formula:

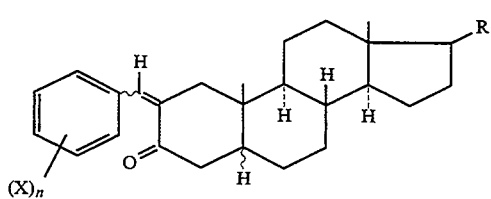

[IV]

or the formula:

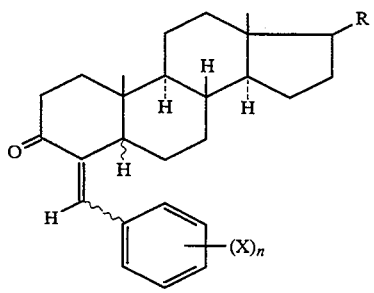

[V]

wherein R is an alkyl group having 1–20 carbon atoms; X is an amino group, an alkylamino group having 1 to 6 carbon atoms, a dialkylamino group having 1 to 6 carbon atoms in each alkyl group, an acylated amino group having 1 to 6 carbon atoms, a hydroxyl group, an alkoxy group having 1 to 6 carbon atoms, a thioalkyl group having 1 to 6 carbon atoms, an alkyl group having 1–20 carbon atoms, a nitro group, a cyano group or a halogen atom, provided that when n is two or more these groups and atoms may be different from one another; the bond shown by~denotes a cis- or trans-position; and n is an integer of 1 to 5.

15. A steroidal ketone compound according to claim 1, which is represented by the formula:

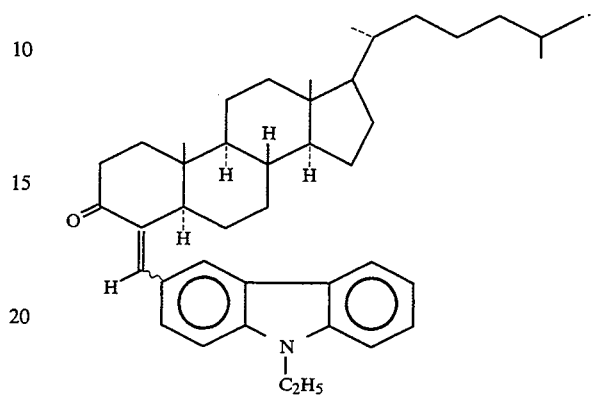

16. A steroidal ketone compound which is represented by the formula:

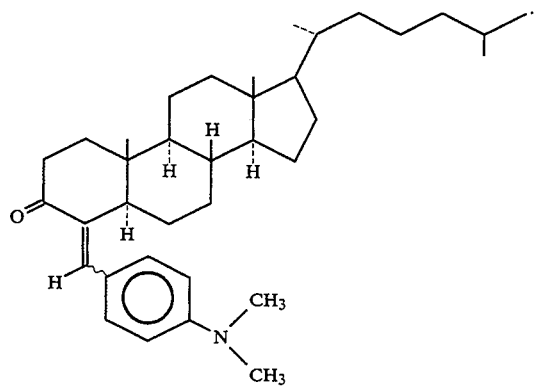

17. A non-linear optical material comprising a steroidal ketone compound of claim 15.

18. A non-linear optical material comprising a steroidal ketone compound of claim 16.

19. A non-linear optical material using the non-linear optical material of claim 17.

20. A non-linear optical material using the non-linear optical material of claim 18.

21. A steroidal ketone compound according to claim 2, wherein R is an alkyl group having 1 to 20 carbon atoms; X is an amino group, an alkylamino group having 1 to 6 carbon atoms, a dialkylamino group having 1 to 6 carbon atoms in each alkyl group, or an acylated amino group having 1 to 6 carbon atoms; and n is an integer of 1 to 5.

22. A steroidal ketone compound according to claim 2 wherein R is an alkyl group having 1 to 20 carbon atoms; X is an alkylamino group having 1 to 6 carbon atoms, and n is an integer of 1 to 5.

23. A steroidal ketone compound represented by the formula:

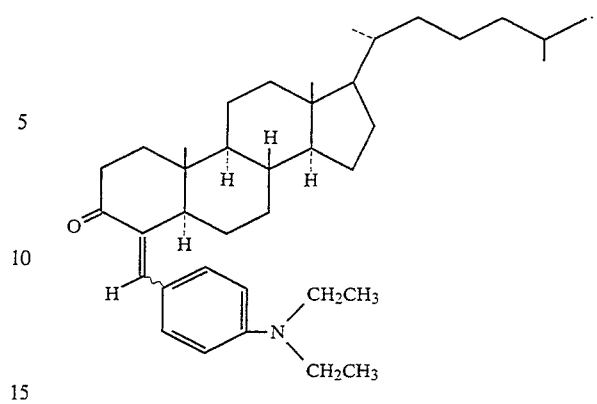
wherein the bond shown by ⁓ denotes a cis- or trans-position.
24. A steroidal ketone compound according to claim 2, wherein the compound is the compound represented by formula (V).
* * * * *